(12) United States Patent
Friedman et al.

(10) Patent No.: US 8,486,376 B2
(45) Date of Patent: Jul. 16, 2013

(54) MOISTURIZING FOAM CONTAINING LANOLIN

(75) Inventors: Doron Friedman, Karmei Yosef (IL); Alex Besonov, Rehovet (IL); Dov Tamarkin, Maccabim (IL); Meir Eini, Ness Ziona (IL)

(73) Assignee: Foamix Ltd., Rehovot (IL)

( * ) Notice: Subject to any disclaimer, the term of this patent is extended or adjusted under 35 U.S.C. 154(b) by 1622 days.

(21) Appl. No.: 11/099,942

(22) Filed: Apr. 6, 2005

(65) Prior Publication Data

US 2005/0244342 A1    Nov. 3, 2005

Related U.S. Application Data

(63) Continuation-in-part of application No. 10/911,367, filed on Aug. 4, 2004, and a continuation-in-part of application No. PCT/IB03/05527, filed on Oct. 24, 2003.

(60) Provisional application No. 60/492,385, filed on Aug. 4, 2003, provisional application No. 60/429,546, filed on Nov. 29, 2002.

(30) Foreign Application Priority Data

Oct. 25, 2002    (IL) .......................................... 152486

(51) Int. Cl.
   *A61K 9/00*    (2006.01)

(52) U.S. Cl.
   USPC ......................................................... 424/47

(58) Field of Classification Search
   None
   See application file for complete search history.

(56) References Cited

U.S. PATENT DOCUMENTS

| | | | |
|---|---|---|---|
| 1,159,250 A | 11/1915 | Moulton | |
| 1,666,684 A | 4/1928 | Carstens | |
| 1,924,972 A | 8/1933 | Beckert | |
| 2,085,733 A | 7/1937 | Bird | |
| 2,390,921 A | 12/1945 | Clark | |
| 2,524,590 A | 10/1950 | Boe | |
| 2,586,287 A | 2/1952 | Apperson | |
| 2,617,754 A | 11/1952 | Neely | |
| 2,767,712 A | 10/1956 | Waterman | |
| 2,968,628 A | 1/1961 | Reed | |
| 3,004,894 A | 10/1961 | Johnson et al. | |
| 3,062,715 A | 11/1962 | Reese | |
| 3,092,255 A | 6/1963 | Hohman | |
| 3,092,555 A | 6/1963 | Horn | |
| 3,067,784 A | 12/1963 | Gorman | |
| 3,141,821 A * | 7/1964 | Compeau ........................ | 424/65 |
| 3,142,420 A | 7/1964 | Gawthrop | |
| 3,144,386 A | 8/1964 | Brighttenback | |
| 3,149,543 A | 9/1964 | Naab | |
| 3,154,075 A | 10/1964 | Weckesser | |
| 3,178,352 A * | 4/1965 | Erickson ......................... | 424/73 |
| 3,236,457 A | 2/1966 | Kennedy et al. | |
| 3,244,589 A | 4/1966 | Sunnen | |
| 3,252,859 A | 5/1966 | Silver | |
| 3,261,695 A | 7/1966 | Sienciewicz | |
| 3,263,867 A | 8/1966 | Lehmann | |
| 3,263,869 A | 8/1966 | Corsette | |
| 3,298,919 A * | 1/1967 | Todd et al. ...................... | 424/47 |
| 3,301,444 A | 1/1967 | Wittke | |
| 3,303,970 A | 2/1967 | Breslau et al. | |
| 3,330,730 A | 7/1967 | Hernaadez | |
| 3,333,333 A | 8/1967 | Noack | |
| 3,346,451 A | 10/1967 | Collins et al. | |
| 3,366,494 A | 1/1968 | Bower | |
| 3,369,034 A | 2/1968 | Chalmers | |
| 3,377,004 A | 4/1968 | Wittke | |
| 3,384,541 A | 5/1968 | Clark et al. | |
| 3,395,214 A | 7/1968 | Mummert | |
| 3,395,215 A | 7/1968 | Warren | |
| 3,401,849 A | 9/1968 | Weber, III | |
| 3,419,658 A | 12/1968 | Amsdon | |
| 3,456,052 A | 7/1969 | Gordon | |
| 3,527,559 A | 9/1970 | Sliwinksi | |
| 3,540,448 A | 11/1970 | Sunnen | |
| 3,559,890 A | 2/1971 | Brooks et al. | |
| 3,561,262 A | 2/1971 | Borocki | |
| 3,563,098 A | 2/1971 | Weber, III | |
| 3,574,821 A | 4/1971 | Pfirrmann et al. | |
| 3,577,518 A | 5/1971 | Shepherd | |
| 3,667,461 A | 6/1972 | Zamarra | |
| 3,751,562 A | 8/1973 | Nichols | |
| 3,770,648 A | 11/1973 | Mackes | |
| 3,787,566 A * | 1/1974 | Gauvreau ........................ | 424/45 |
| 3,819,524 A | 6/1974 | Schubert et al. | |
| 3,841,525 A | 10/1974 | Siegel | |
| 3,849,580 A | 11/1974 | Weinstein et al. | |
| 3,865,275 A | 2/1975 | De Nunzio | |

(Continued)

FOREIGN PATENT DOCUMENTS

| AU | 198780257 | 9/1986 |
|---|---|---|
| CA | 2422244 | 9/2003 |

(Continued)

OTHER PUBLICATIONS

Galligan et al. Journal of Dental Research 47(4):629-632; 1968.*

(Continued)

*Primary Examiner* — David J Blanchard
*Assistant Examiner* — Garen Gotfredson
(74) *Attorney, Agent, or Firm* — Fish & Richardson P.C.

(57) ABSTRACT

The present invention provides a highly tolerable, hydrating lanolin containing foamable composition for administration to the skin, body surface, body cavity or mucosal surface, e.g., the mucosa of the nose, mouth, eye, ear, respiratory system, vagina or rectum. The foamable composition includes lanolin, a surface-active agent, about 0.01% to about 5% by weight of at least one polymeric additive selected from the group consisting of a bioadhesive agent, a gelling agent, a film forming agent and a phase change agent, water, and a liquefied or compressed gas propellant at a concentration of about 3% to about 25% by weight of the total composition.

36 Claims, 2 Drawing Sheets

U.S. PATENT DOCUMENTS

| | | | |
|---|---|---|---|
| 3,866,800 A | 2/1975 | Schmitt | |
| 3,882,228 A | 5/1975 | Boncey et al. | |
| 3,886,084 A | 5/1975 | Vassiliades | |
| 3,890,305 A | 6/1975 | Weber et al. | |
| 3,912,665 A | 10/1975 | Spitzer et al. | |
| 3,923,970 A | 12/1975 | Breuer | |
| 3,929,985 A | 12/1975 | Webb, Jr. | |
| 3,952,916 A | 4/1976 | Phillips | |
| 3,959,160 A | 5/1976 | Horsler et al. | |
| 3,962,150 A | 6/1976 | Viola | |
| 3,963,833 A | 6/1976 | DeSalva et al. | |
| 3,966,090 A | 6/1976 | Prussin et al. | |
| 3,966,632 A | 6/1976 | Colliopoulos et al. | |
| 3,970,219 A | 7/1976 | Spitzer et al. | |
| 3,970,584 A | 7/1976 | Hart et al. | |
| 3,993,224 A | 11/1976 | Harrison | |
| 3,997,467 A | 12/1976 | Jederstrom et al. | |
| 4,001,391 A | 1/1977 | Feinstone et al. | |
| 4,001,442 A | 1/1977 | Stahlberger et al. | |
| 4,018,396 A | 4/1977 | Showmaker et al. | |
| 4,019,657 A | 4/1977 | Spitzer et al. | |
| 4,083,974 A | 4/1978 | Turi | |
| 4,100,426 A | 7/1978 | Baranowski | |
| 4,102,995 A | 7/1978 | Hebborn | |
| 4,110,426 A | 8/1978 | Barnhurst et al. | |
| 4,124,149 A | 11/1978 | Spitzer et al. | |
| 4,145,411 A | 3/1979 | Mende | |
| 4,151,272 A | 4/1979 | Geary et al. | |
| 4,160,827 A | 7/1979 | Cho et al. | |
| 4,213,979 A | 7/1980 | Levine | |
| 4,214,000 A * | 7/1980 | Papa | 514/494 |
| 4,226,344 A | 10/1980 | Booth et al. | |
| 4,229,432 A | 10/1980 | Geria | |
| 4,230,701 A | 10/1980 | Holick et al. | |
| 4,241,048 A | 12/1980 | Durbak et al. | |
| 4,241,149 A | 12/1980 | Labes et al. | |
| 4,252,787 A | 2/1981 | Sherman et al. | |
| 4,254,104 A | 3/1981 | Suzuki et al. | |
| 4,268,499 A | 5/1981 | Keil | |
| 4,271,149 A | 6/1981 | Winicov et al. | |
| 4,292,250 A | 9/1981 | DeLuca et al. | |
| 4,292,326 A | 9/1981 | Nazzaro-Porro et al. | |
| 4,299,826 A | 11/1981 | Luedders | |
| 4,305,936 A | 12/1981 | Klein | |
| 4,309,995 A | 1/1982 | Sacco | |
| 4,310,510 A | 1/1982 | Sherman et al. | |
| 4,323,694 A | 4/1982 | Scala, Jr. | |
| 4,325,939 A | 4/1982 | Shah | |
| 4,329,990 A | 5/1982 | Sneider | |
| 4,335,120 A | 6/1982 | Holick et al. | |
| 4,352,808 A | 10/1982 | Rane et al. | |
| 4,385,161 A | 5/1983 | Caunt et al. | |
| 4,386,104 A | 5/1983 | Nazzaro-Porro | |
| 4,393,066 A | 7/1983 | Garrett et al. | |
| 4,427,670 A | 1/1984 | Ofuchi et al. | |
| 4,439,416 A | 3/1984 | Cordon et al. | |
| 4,439,441 A * | 3/1984 | Hallesy et al. | 514/396 |
| 4,440,320 A | 4/1984 | Wernicke | |
| 4,447,486 A | 5/1984 | Hoppe et al. | |
| 4,469,674 A | 9/1984 | Shah et al. | |
| 4,508,705 A | 4/1985 | Chaudhuri et al. | |
| 4,522,948 A * | 6/1985 | Walker | 514/396 |
| 4,529,601 A | 7/1985 | Broberg et al. | |
| 4,529,605 A * | 7/1985 | Lynch et al. | 514/552 |
| 4,552,872 A | 11/1985 | Cooper et al. | |
| 4,574,052 A | 3/1986 | Gupte et al. | |
| 4,576,961 A * | 3/1986 | Lorck et al. | 514/462 |
| 4,595,526 A | 6/1986 | Lai | |
| 4,603,812 A | 8/1986 | Stoesser et al. | |
| 4,627,973 A | 12/1986 | Moran et al. | |
| 4,628,063 A | 12/1986 | Haines et al. | |
| 4,661,524 A | 4/1987 | Thomson et al. | |
| 4,672,078 A | 6/1987 | Sakai et al. | |
| 4,673,569 A | 6/1987 | Shernov et al. | |
| 4,678,463 A | 7/1987 | Millar | |
| 4,701,320 A | 10/1987 | Hasegawa et al. | |
| 4,725,609 A | 2/1988 | Kull, Jr. et al. | |
| 4,738,396 A | 4/1988 | Doi et al. | |
| 4,741,855 A | 5/1988 | Grote et al. | |
| 4,752,465 A | 6/1988 | Mackles | |
| 4,770,634 A | 9/1988 | Pellico | |
| 4,780,309 A | 10/1988 | Geria et al. | |
| 4,784,842 A | 11/1988 | London et al. | |
| 4,792,062 A | 12/1988 | Goncalves et al. | |
| 4,798,682 A | 1/1989 | Ansmann | |
| 4,804,674 A | 2/1989 | Curtis-Prior | |
| 4,806,262 A | 2/1989 | Snyder | |
| 4,808,388 A | 2/1989 | Beutler et al. | |
| 4,822,613 A | 4/1989 | Rodero | |
| 4,822,614 A | 4/1989 | Rodero | |
| 4,826,048 A | 5/1989 | Skorka et al. | |
| 4,827,378 A | 5/1989 | Gillan et al. | |
| 4,828,837 A | 5/1989 | Uster et al. | |
| 4,836,217 A | 6/1989 | Fischer et al. | |
| 4,837,019 A | 6/1989 | Georgalas et al. | |
| 4,837,378 A | 6/1989 | Borgman | |
| 4,844,902 A | 7/1989 | Grohe | |
| 4,847,068 A | 7/1989 | Dole et al. | |
| 4,849,117 A * | 7/1989 | Bronner et al. | 252/3 |
| 4,855,294 A | 8/1989 | Patel et al. | |
| 4,863,900 A | 9/1989 | Pollock et al. | |
| 4,867,967 A | 9/1989 | Crutcher | |
| 4,873,078 A | 10/1989 | Edmundson et al. | |
| 4,874,794 A | 10/1989 | Katz | |
| 4,877,805 A | 10/1989 | Kligman | |
| 4,885,282 A | 12/1989 | Thornfeldt | |
| 4,897,262 A | 1/1990 | Nandagiri et al. | |
| 4,902,281 A | 2/1990 | Avoy | |
| 4,906,453 A | 3/1990 | Tsoucalas | |
| 4,913,893 A | 4/1990 | Varco et al. | |
| 4,919,934 A | 4/1990 | Deckner et al. | |
| 4,954,487 A | 9/1990 | Cooper et al. | |
| 4,956,049 A | 9/1990 | Bernheim et al. | |
| 4,957,732 A * | 9/1990 | Grollier et al. | 424/73 |
| 4,963,351 A | 10/1990 | Weston | |
| 4,966,779 A | 10/1990 | Kirk | |
| 4,970,067 A | 11/1990 | Panandiker et al. | |
| 4,975,466 A | 12/1990 | Bottcher et al. | |
| 4,981,367 A | 1/1991 | Brazelton | |
| 4,981,677 A | 1/1991 | Thau | |
| 4,981,679 A | 1/1991 | Briggs et al. | |
| 4,981,845 A | 1/1991 | Pereira et al. | |
| 4,985,459 A | 1/1991 | Sunshine et al. | |
| 4,992,478 A | 2/1991 | Geria | |
| 4,993,496 A | 2/1991 | Riedle et al. | |
| 5,002,540 A | 3/1991 | Brodman et al. | |
| 5,002,680 A | 3/1991 | Schmidt et al. | |
| 5,007,556 A | 4/1991 | Lover | |
| 5,013,297 A | 5/1991 | Cattanach | |
| 5,015,471 A | 5/1991 | Birtwistle et al. | |
| 5,019,375 A | 5/1991 | Tanner et al. | |
| 5,034,220 A | 7/1991 | Helioff et al. | |
| 5,035,895 A | 7/1991 | Shibusawa et al. | |
| 5,053,228 A | 10/1991 | Mori et al. | |
| 5,071,648 A | 12/1991 | Rosenblatt | |
| 5,071,881 A | 12/1991 | Parfondry et al. | |
| 5,073,371 A | 12/1991 | Turner et al. | |
| 5,082,651 A | 1/1992 | Healey et al. | |
| 5,087,618 A | 2/1992 | Bodor | |
| 5,089,252 A | 2/1992 | Grollier et al. | |
| 5,091,111 A | 2/1992 | Neumiller | |
| 5,094,853 A | 3/1992 | Hagarty | |
| 5,100,917 A | 3/1992 | Flynn et al. | |
| 5,104,645 A | 4/1992 | Cardin et al. | |
| 5,112,359 A | 5/1992 | Murphy et al. | |
| 5,114,718 A | 5/1992 | Damani | |
| 5,122,519 A | 6/1992 | Ritter | |
| 5,130,121 A | 7/1992 | Kopolow et al. | |
| 5,133,972 A | 7/1992 | Ferrini et al. | |
| 5,135,915 A | 8/1992 | Czarniecki et al. | |
| 5,137,714 A | 8/1992 | Scott | |
| 5,143,717 A | 9/1992 | Davis | |
| 5,156,765 A | 10/1992 | Smrt | |
| 5,164,357 A | 11/1992 | Bartman et al. | |
| 5,164,367 A | 11/1992 | Pickart | |
| 5,167,950 A | 12/1992 | Lins | |
| 5,171,577 A | 12/1992 | Griat et al. | |

| Patent No. | Date | Inventor |
|---|---|---|
| 5,196,405 A | 3/1993 | Packman |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A * | 1/1994 | Hayes ............... 424/73 |
| 5,286,475 A | 2/1994 | Louvet et al. |
| 5,300,286 A * | 4/1994 | Gee ............... 424/78.03 |
| 5,301,841 A | 4/1994 | Fuchs et al. |
| 5,308,643 A | 5/1994 | Osipow et al. |
| 5,314,904 A | 5/1994 | Egidio et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo |
| 5,384,308 A | 1/1995 | Henkin |
| 5,385,943 A | 1/1995 | Nazzaro-Porro |
| 5,389,676 A | 2/1995 | Michaels |
| 5,397,312 A | 3/1995 | Rademaker et al. |
| 5,398,846 A | 3/1995 | Corba et al. |
| 5,399,205 A * | 3/1995 | Shinohara et al. ............... 134/40 |
| 5,411,992 A | 5/1995 | Eini et al. |
| 5,422,361 A * | 6/1995 | Munayyer et al. ............ 514/408 |
| 5,429,815 A | 7/1995 | Faryniarz et al. |
| 5,435,996 A | 7/1995 | Glover et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A * | 4/1996 | Briand .................... 424/195.17 |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,700,396 A | 12/1997 | Suzuki et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda et al. |
| 5,730,964 A | 3/1998 | Waldstreicher |
| 5,733,558 A | 3/1998 | Breton et al. |
| 5,733,572 A | 3/1998 | Unger et al. |
| 5,747,049 A | 5/1998 | Tominaga |
| 5,753,241 A | 5/1998 | Ribier et al. |
| 5,753,245 A | 5/1998 | Fowler et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A * | 11/1998 | Oldham et al. ................... 514/2 |
| 5,843,411 A | 12/1998 | Hernandez et al. |
| 5,846,983 A | 12/1998 | Sandborn et al. |
| 5,849,042 A | 12/1998 | Lim et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton |
| 5,902,574 A * | 5/1999 | Stoner et al. .................... 424/73 |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,922,331 A | 7/1999 | Mausner |
| 5,925,669 A | 7/1999 | Katz et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |

| | | |
|---|---|---|
| 5,993,846 A | 11/1999 | Friedman et al. |
| 6,001,341 A | 12/1999 | Genova et al. |
| 6,006,948 A | 12/1999 | Auer |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |
| 6,045,779 A | 4/2000 | Mueller et al. |
| 6,071,536 A | 6/2000 | Suzuki et al. |
| 6,075,056 A | 6/2000 | Quigley, Jr. et al. |
| 6,080,394 A | 6/2000 | Lin et al. |
| 6,087,317 A | 7/2000 | Gee |
| 6,090,772 A | 7/2000 | Kaiser et al. |
| 6,093,408 A | 7/2000 | Hasenoehrl et al. |
| 6,096,756 A | 8/2000 | Crain et al. |
| 6,110,477 A | 8/2000 | Hernandez et al. |
| 6,110,966 A | 8/2000 | Pollock |
| 6,113,888 A | 9/2000 | Castro et al. |
| 6,116,466 A | 9/2000 | Gueret et al. |
| 6,121,210 A | 9/2000 | Taylor |
| 6,126,920 A | 10/2000 | Jones et al. |
| 6,140,355 A | 10/2000 | Egidio et al. |
| 6,146,645 A | 11/2000 | Deckers et al. |
| 6,146,664 A | 11/2000 | Siddiqui |
| 6,162,834 A | 12/2000 | Sebillotte-Arnaud et al. |
| 6,165,455 A | 12/2000 | Torgerson et al. |
| 6,168,576 B1 | 1/2001 | Reynolds |
| 6,171,347 B1 | 1/2001 | Kunz et al. |
| 6,180,669 B1 | 1/2001 | Tamarkin |
| 6,183,762 B1 | 2/2001 | Deckers et al. |
| 6,186,367 B1 | 2/2001 | Harrold |
| 6,187,290 B1 | 2/2001 | Gilchrist et al. |
| 6,189,810 B1 | 2/2001 | Nerushai et al. |
| 6,190,365 B1 | 2/2001 | Abbott et al. |
| 6,204,285 B1 | 3/2001 | Fabiano et al. |
| 6,210,656 B1 | 4/2001 | Touzan et al. |
| 6,210,742 B1 | 4/2001 | Deckers et al. |
| 6,214,318 B1 | 4/2001 | Osipow et al. |
| 6,214,788 B1 | 4/2001 | Velazco et al. |
| 6,221,381 B1 | 4/2001 | Shelford et al. |
| 6,221,823 B1 * | 4/2001 | Crisanti et al. ............ 510/238 |
| 6,224,888 B1 | 5/2001 | Vatter et al. |
| 6,231,837 B1 | 5/2001 | Stroud et al. |
| 6,232,315 B1 | 5/2001 | Shafer et al. |
| 6,251,369 B1 | 6/2001 | Stoltz |
| 6,258,374 B1 | 7/2001 | Friess et al. |
| 6,271,295 B1 | 8/2001 | Powell et al. |
| 6,274,150 B1 | 8/2001 | Simonnet et al. |
| 6,287,546 B1 * | 9/2001 | Reich et al. ............ 424/70.121 |
| 6,294,550 B1 | 9/2001 | Place et al. |
| 6,299,023 B1 | 10/2001 | Arnone |
| 6,299,032 B1 | 10/2001 | Hamilton |
| 6,299,900 B1 | 10/2001 | Reed et al. |
| 6,305,578 B1 | 10/2001 | Hildebrandt et al. |
| 6,306,841 B1 | 10/2001 | Place et al. |
| 6,308,863 B1 | 10/2001 | Harman |
| 6,319,913 B1 | 11/2001 | Mak et al. |
| 6,328,950 B1 | 12/2001 | Franzke et al. |
| 6,328,982 B1 | 12/2001 | Shiroyama et al. |
| 6,333,362 B1 | 12/2001 | Lorant |
| 6,335,022 B1 | 1/2002 | Simonnet et al. |
| 6,341,717 B2 | 1/2002 | Auer |
| 6,344,218 B1 | 2/2002 | Dodd et al. |
| 6,348,229 B1 | 2/2002 | Eini et al. |
| 6,358,541 B1 | 3/2002 | Goodman |
| 6,364,854 B1 | 4/2002 | Ferrer et al. |
| 6,372,234 B1 | 4/2002 | Deckers et al. |
| 6,375,960 B1 | 4/2002 | Simonnet et al. |
| 6,383,471 B1 | 5/2002 | Chen et al. |
| 6,395,258 B1 | 5/2002 | Steer |
| 6,395,300 B1 * | 5/2002 | Straub et al. ............ 424/489 |
| 6,403,061 B1 | 6/2002 | Candau et al. |
| 6,403,069 B1 | 6/2002 | Chopra et al. |
| 6,410,036 B1 | 6/2002 | De Rosa et al. |
| 6,423,323 B2 | 7/2002 | Neubourg |
| 6,428,772 B1 | 8/2002 | Singh et al. |
| 6,433,003 B1 | 8/2002 | Bobrove et al. |
| 6,433,024 B1 | 8/2002 | Popp et al. |
| 6,433,033 B1 | 8/2002 | Isobe et al. |
| 6,437,006 B1 | 8/2002 | Yoon et al. |
| 6,440,429 B1 | 8/2002 | Torizuka et al. |
| 6,447,801 B1 | 9/2002 | Salafsky et al. |
| 6,455,076 B1 | 9/2002 | Hahn et al. |
| 6,468,989 B1 | 10/2002 | Chang |
| 6,479,058 B1 | 11/2002 | McCadden |
| 6,486,168 B1 | 11/2002 | Skwierczynski et al. |
| 6,488,947 B1 | 12/2002 | Bekele |
| 6,511,655 B1 | 1/2003 | Muller et al. |
| 6,514,487 B1 | 2/2003 | Barr |
| 6,524,594 B1 | 2/2003 | Santora et al. |
| 6,531,118 B1 | 3/2003 | Gonzalez et al. |
| 6,534,455 B1 | 3/2003 | Maurin et al. |
| 6,536,629 B2 | 3/2003 | van der Heijden |
| 6,544,530 B1 | 4/2003 | Friedman |
| 6,544,562 B2 | 4/2003 | Singh et al. |
| 6,547,063 B1 | 4/2003 | Zaveri et al. |
| 6,548,074 B1 | 4/2003 | Mohammadi |
| 6,562,355 B1 | 5/2003 | Renault |
| 6,566,350 B2 | 5/2003 | Ono et al. |
| 6,582,679 B2 | 6/2003 | Stein et al. |
| 6,582,710 B2 | 6/2003 | Deckers et al. |
| 6,589,509 B2 | 7/2003 | Keller et al. |
| 6,596,287 B2 | 7/2003 | Deckers et al. |
| 6,599,513 B2 | 7/2003 | Deckers et al. |
| 6,620,773 B1 | 9/2003 | Stork et al. |
| 6,638,981 B2 | 10/2003 | Williams et al. |
| 6,649,571 B1 | 11/2003 | Morgan |
| 6,649,574 B2 | 11/2003 | Cardis et al. |
| 6,672,483 B1 | 1/2004 | Roy et al. |
| 6,682,726 B2 | 1/2004 | Marchesi et al. |
| 6,691,898 B2 | 2/2004 | Hurray et al. |
| 6,709,663 B2 | 3/2004 | Espinoza |
| 6,723,309 B1 | 4/2004 | Deane |
| 6,730,288 B1 | 5/2004 | Abram |
| 6,753,000 B2 | 6/2004 | Breton et al. |
| 6,753,167 B2 | 6/2004 | Moloney et al. |
| 6,762,158 B2 | 7/2004 | Lukenbach et al. |
| 6,765,001 B2 | 7/2004 | Gans et al. |
| 6,774,114 B2 | 8/2004 | Castiel et al. |
| 6,777,591 B1 | 8/2004 | Chaudhary et al. |
| 6,790,435 B1 | 9/2004 | Ma et al. |
| 6,796,973 B1 | 9/2004 | Contente et al. |
| RE38,623 E | 10/2004 | Hernandez et al. |
| 6,811,767 B1 | 11/2004 | Bosch et al. |
| 6,834,778 B2 | 12/2004 | Jinbo et al. |
| 6,843,390 B1 | 1/2005 | Bristor |
| 6,875,438 B2 | 4/2005 | Kraemer et al. |
| 6,881,271 B2 | 4/2005 | Ochiai |
| 6,890,567 B2 | 5/2005 | Nakatsu et al. |
| 6,902,737 B2 | 6/2005 | Quemin et al. |
| 6,911,211 B2 | 6/2005 | Eini et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Brandt et al. |
| 6,967,012 B2 | 11/2005 | Eini et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram et al. |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |

| | | | | | |
|---|---|---|---|---|---|
| 7,270,828 B2 | 9/2007 | Masuda et al. | 2004/0191196 A1 | 9/2004 | Tamarkin |
| 7,455,195 B2 | 11/2008 | Mekata | 2004/0192754 A1 | 9/2004 | Shapira et al. |
| 7,497,354 B2 | 3/2009 | Decottignies et al. | 2004/0195276 A1 | 10/2004 | Fuchs |
| 7,575,739 B2 | 8/2009 | Tamarkin et al. | 2004/0197276 A1 | 10/2004 | Takase et al. |
| 7,645,803 B2 | 1/2010 | Tamarkin et al. | 2004/0197295 A1 | 10/2004 | Riedel et al. |
| 7,654,415 B2 | 2/2010 | van der Heijden | 2004/0219122 A1 | 11/2004 | Masuda et al. |
| 7,682,523 B2 | 3/2010 | Eini et al. | 2004/0219176 A1 | 11/2004 | Dominguez |
| 7,682,623 B2 | 3/2010 | Eini et al. | 2004/0220187 A1 | 11/2004 | Stephenson et al. |
| 7,700,076 B2 | 4/2010 | Tamarkin et al. | 2004/0229813 A1 | 11/2004 | DiPiano et al. |
| 7,704,518 B2 | 4/2010 | Tamarkin et al. | 2004/0234475 A1 | 11/2004 | Lannibois-Drean et al. |
| 7,793,807 B2 | 9/2010 | Goujon et al. | 2004/0241099 A1 | 12/2004 | Popp |
| 7,960,416 B2 | 6/2011 | Sato et al. | 2004/0247531 A1 | 12/2004 | Riedel et al. |
| 2001/0006654 A1 | 7/2001 | Cannell et al. | 2004/0253275 A1 | 12/2004 | Eini et al. |
| 2001/0027218 A1 | 10/2001 | Stern et al. | 2004/0258627 A1 | 12/2004 | Riedel et al. |
| 2001/0027981 A1 | 10/2001 | Vlodek | 2004/0265240 A1 | 12/2004 | Tamarkin et al. |
| 2001/0036450 A1 | 11/2001 | Verite et al. | 2005/0002976 A1 | 1/2005 | Wu |
| 2002/0002151 A1 | 1/2002 | Ono et al. | 2005/0013853 A1 | 1/2005 | Gil-Ad et al. |
| 2002/0004063 A1 | 1/2002 | Zhang | 2005/0031547 A1* | 2/2005 | Tamarkin et al. ............... 424/45 |
| 2002/0013481 A1 | 1/2002 | Schonrock et al. | 2005/0042182 A1 | 2/2005 | Arkin |
| 2002/0015721 A1 | 2/2002 | Simonnet et al. | 2005/0054991 A1 | 3/2005 | Tobyn et al. |
| 2002/0032171 A1* | 3/2002 | Chen et al. ...................... 514/54 | 2005/0069566 A1 | 3/2005 | Tamarkin et al. |
| 2002/0035046 A1 | 3/2002 | Lukenbach et al. | 2005/0074414 A1 | 4/2005 | Tamarkin et al. |
| 2002/0035070 A1 | 3/2002 | Gardlik et al. | 2005/0075407 A1 | 4/2005 | Tamarkin et al. |
| 2002/0035087 A1 | 3/2002 | Barclay | 2005/0079139 A1 | 4/2005 | Jacques et al. |
| 2002/0035182 A1 | 3/2002 | L'Alloret et al. | 2005/0084551 A1 | 4/2005 | Jensen et al. |
| 2002/0039591 A1 | 4/2002 | Dahle | 2005/0085843 A1 | 4/2005 | Opolski et al. |
| 2002/0044659 A1 | 4/2002 | Ohta | 2005/0101936 A1 | 5/2005 | Gonzales et al. |
| 2002/0045659 A1 | 4/2002 | Michelet et al. | 2005/0106197 A1 | 5/2005 | Blin et al. |
| 2002/0048798 A1 | 4/2002 | Avery et al. | 2005/0123494 A1 | 6/2005 | Swaile et al. |
| 2002/0058010 A1 | 5/2002 | Picard-Lesboueyries et al. | 2005/0123496 A1 | 6/2005 | Shah et al. |
| 2002/0072544 A1 | 6/2002 | Miller et al. | 2005/0186142 A1 | 8/2005 | Tamarkin et al. |
| 2002/0090386 A1 | 7/2002 | Haslwanter et al. | 2005/0186147 A1* | 8/2005 | Tamarkin et al. ............... 424/47 |
| 2002/0098215 A1 | 7/2002 | Douin et al. | 2005/0189377 A1 | 9/2005 | Lanzendorfer et al. |
| 2002/0111281 A1 | 8/2002 | Vishnupad | 2005/0196414 A1 | 9/2005 | Dake et al. |
| 2002/0117516 A1 | 8/2002 | Lasserre et al. | 2005/0205086 A1 | 9/2005 | Tamarkin et al. |
| 2002/0134376 A1 | 9/2002 | Castro et al. | 2005/0207837 A1 | 9/2005 | Kosh et al. |
| 2002/0136755 A1 | 9/2002 | Tyrrell et al. | 2005/0222090 A1 | 10/2005 | Cheng et al. |
| 2002/0143188 A1 | 10/2002 | Garvey et al. | 2005/0232869 A1 | 10/2005 | Tamarkin et al. |
| 2002/0153390 A1 | 10/2002 | Vlodek | 2005/0244342 A1 | 11/2005 | Friedman et al. |
| 2002/0165170 A1 | 11/2002 | Wilson et al. | 2005/0244354 A1 | 11/2005 | Speron |
| 2002/0182162 A1 | 12/2002 | Shahinpoor et al. | 2005/0245902 A1 | 11/2005 | Cornish et al. |
| 2002/0187181 A1 | 12/2002 | Godbey et al. | 2005/0252995 A1 | 11/2005 | Westphal et al. |
| 2002/0198136 A1 | 12/2002 | Mak et al. | 2005/0255048 A1 | 11/2005 | Hirsh et al. |
| 2003/0006193 A1 | 1/2003 | Ikeda et al. | 2005/0258189 A1 | 11/2005 | Peterson et al. |
| 2003/0031693 A1 | 2/2003 | Breton et al. | 2005/0266035 A1 | 12/2005 | Healy et al. |
| 2003/0053961 A1 | 3/2003 | Eccard | 2005/0268416 A1 | 12/2005 | Sommers |
| 2003/0077297 A1 | 4/2003 | Chen et al. | 2005/0271596 A1* | 12/2005 | Friedman et al. ............... 424/45 |
| 2003/0078172 A1 | 4/2003 | Guiramand et al. | 2005/0271598 A1* | 12/2005 | Friedman et al. ............... 424/47 |
| 2003/0114520 A1 | 6/2003 | Pereira et al. | 2005/0276836 A1 | 12/2005 | Wilson et al. |
| 2003/0118515 A1 | 6/2003 | Jew et al. | 2005/0281755 A1 | 12/2005 | Zarif et al. |
| 2003/0130247 A1 | 7/2003 | Gans et al. | 2005/0281766 A1 | 12/2005 | Martin et al. |
| 2003/0175232 A1 | 9/2003 | Elliott et al. | 2005/0285912 A1 | 12/2005 | Delametter et al. |
| 2003/0175315 A1 | 9/2003 | Yoo et al. | 2005/0287081 A1 | 12/2005 | Aust et al. |
| 2003/0180347 A1 | 9/2003 | Young et al. | 2006/0008432 A1 | 1/2006 | Scarampi et al. |
| 2003/0185839 A1 | 10/2003 | Podolsky | 2006/0014990 A1 | 1/2006 | Kuechler et al. |
| 2003/0194379 A1 | 10/2003 | Brugger et al. | 2006/0018937 A1* | 1/2006 | Friedman et al. ............. 424/401 |
| 2003/0195128 A1 | 10/2003 | Deckman et al. | 2006/0018938 A1 | 1/2006 | Neubourg |
| 2003/0206955 A1 | 11/2003 | Sonneville-Aubrun et al. | 2006/0029565 A1 | 2/2006 | Xu et al. |
| 2003/0215472 A1 | 11/2003 | Bonda et al. | 2006/0051301 A1 | 3/2006 | Galopin et al. |
| 2004/0018228 A1 | 1/2004 | Fischell et al. | 2006/0054634 A1 | 3/2006 | Mekata |
| 2004/0028752 A1 | 2/2004 | Kamm et al. | 2006/0057168 A1 | 3/2006 | Larm |
| 2004/0038912 A1 | 2/2004 | Michelet et al. | 2006/0088561 A1 | 4/2006 | Eini et al. |
| 2004/0053797 A1* | 3/2004 | Chen et al. ................... 510/130 | 2006/0099151 A1 | 5/2006 | Neubourg |
| 2004/0058878 A1 | 3/2004 | Walker | 2006/0108377 A1 | 5/2006 | Glynn et al. |
| 2004/0063787 A1 | 4/2004 | Villanueva | 2006/0110418 A1 | 5/2006 | Johnson |
| 2004/0067970 A1 | 4/2004 | Foster et al. | 2006/0114745 A1 | 6/2006 | Ollmann et al. |
| 2004/0072638 A1 | 4/2004 | Enos et al. | 2006/0121073 A1 | 6/2006 | Goyal et al. |
| 2004/0076651 A1 | 4/2004 | Brocks et al. | 2006/0140984 A1 | 6/2006 | Tamarkin et al. |
| 2004/0078896 A1 | 4/2004 | Hellyer et al. | 2006/0140990 A1 | 6/2006 | Bortz et al. |
| 2004/0079361 A1 | 4/2004 | Clayton et al. | 2006/0160713 A1 | 7/2006 | Sekine et al. |
| 2004/0105825 A1 | 6/2004 | Henning | 2006/0165616 A1 | 7/2006 | Brock et al. |
| 2004/0120917 A1 | 6/2004 | Perrier et al. | 2006/0177392 A1 | 8/2006 | Walden |
| 2004/0127554 A1 | 7/2004 | Ghisalberti | 2006/0193789 A1 | 8/2006 | Tamarkin et al. |
| 2004/0138179 A1 | 7/2004 | Goldstein et al. | 2006/0193813 A1 | 8/2006 | Simonnet |
| 2004/0151671 A1 | 8/2004 | Abram et al. | 2006/0204446 A1 | 9/2006 | Lulla et al. |
| 2004/0151756 A1 | 8/2004 | Richards et al. | 2006/0222675 A1 | 10/2006 | Sabnis et al. |
| 2004/0161447 A1 | 8/2004 | Paul | 2006/0233721 A1* | 10/2006 | Tamarkin et al. ............... 424/47 |
| 2004/0184992 A1 | 9/2004 | Abram | 2006/0239937 A2 | 10/2006 | Neubourg |
| 2004/0185123 A1 | 9/2004 | Mazzio et al. | 2006/0251684 A1 | 11/2006 | Annis et al. |

| Publication No. | Date | Name |
|---|---|---|
| 2006/0254597 A1 | 11/2006 | Thompson |
| 2006/0263323 A1 | 11/2006 | Hoang et al. |
| 2006/0269485 A1* | 11/2006 | Friedman et al. ............... 424/45 |
| 2006/0272199 A1* | 12/2006 | Licciardello et al. ........... 44/275 |
| 2006/0275218 A1* | 12/2006 | Tamarkin et al. ............... 424/45 |
| 2006/0275221 A1 | 12/2006 | Tamarkin et al. |
| 2006/0285912 A1 | 12/2006 | Eini et al. |
| 2006/0292080 A1 | 12/2006 | Abram et al. |
| 2007/0009607 A1 | 1/2007 | Jones |
| 2007/0017696 A1 | 1/2007 | Lin et al. |
| 2007/0020213 A1* | 1/2007 | Tamarkin et al. ............ 424/70.1 |
| 2007/0020304 A1 | 1/2007 | Tamarkin et al. |
| 2007/0027055 A1 | 2/2007 | Koivisto et al. |
| 2007/0036831 A1 | 2/2007 | Baker |
| 2007/0059253 A1 | 3/2007 | Popp et al. |
| 2007/0069046 A1 | 3/2007 | Eini et al. |
| 2007/0071688 A1 | 3/2007 | Illel et al. |
| 2007/0098647 A1 | 5/2007 | Neubourg |
| 2007/0134174 A1 | 6/2007 | Irwin et al. |
| 2007/0140999 A1 | 6/2007 | Puglia et al. |
| 2007/0142263 A1 | 6/2007 | Stahl et al. |
| 2007/0148112 A1 | 6/2007 | Dingley et al. |
| 2007/0148194 A1 | 6/2007 | Amiji et al. |
| 2007/0154402 A1 | 7/2007 | Trumbore et al. |
| 2007/0160548 A1 | 7/2007 | Riccardi et al. |
| 2007/0237724 A1 | 10/2007 | Abram et al. |
| 2007/0253911 A1 | 11/2007 | Tamarkin et al. |
| 2007/0264317 A1 | 11/2007 | Yosha et al. |
| 2007/0271235 A1 | 11/2007 | Frank et al. |
| 2007/0280891 A1 | 12/2007 | Tamarkin et al. |
| 2007/0281999 A1 | 12/2007 | Fox et al. |
| 2007/0292355 A1 | 12/2007 | Tamarkin et al. |
| 2007/0292359 A1 | 12/2007 | Friedman et al. |
| 2007/0292461 A1 | 12/2007 | Tamarkin et al. |
| 2008/0008397 A1 | 1/2008 | Kisilev |
| 2008/0015263 A1 | 1/2008 | Bolotin et al. |
| 2008/0015271 A1 | 1/2008 | Abram et al. |
| 2008/0031907 A1 | 2/2008 | Tamarkin et al. |
| 2008/0031908 A1 | 2/2008 | Aubrun-Sonneville et al. |
| 2008/0035155 A1 | 2/2008 | Dahl |
| 2008/0044444 A1 | 2/2008 | Tamarkin et al. |
| 2008/0058055 A1 | 3/2008 | LeMay et al. |
| 2008/0063682 A1 | 3/2008 | Cashman et al. |
| 2008/0069779 A1 | 3/2008 | Tamarkin et al. |
| 2008/0131378 A1 | 6/2008 | Keller et al. |
| 2008/0138293 A1 | 6/2008 | Tamarkin et al. |
| 2008/0138296 A1 | 6/2008 | Tamarkin et al. |
| 2008/0152596 A1 | 6/2008 | Friedman et al. |
| 2008/0153789 A1 | 6/2008 | Dmowski et al. |
| 2008/0166303 A1 | 7/2008 | Tamarkin et al. |
| 2008/0167376 A1 | 7/2008 | Bar-Or et al. |
| 2008/0181854 A1 | 7/2008 | Eini et al. |
| 2008/0188445 A1 | 8/2008 | Muldoon et al. |
| 2008/0188446 A1 | 8/2008 | Muldoon et al. |
| 2008/0193762 A1 | 8/2008 | Dubertret et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0241079 A1 | 10/2008 | Neubourg |
| 2008/0253973 A1 | 10/2008 | Tamarkin et al. |
| 2008/0255498 A1 | 10/2008 | Houle |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0311167 A1 | 12/2008 | Oronsky et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0093514 A1 | 4/2009 | Statham et al. |
| 2009/0130029 A1 | 5/2009 | Tamarkin et al. |
| 2009/0131488 A1 | 5/2009 | Harel et al. |
| 2009/0175799 A1 | 7/2009 | Tamarkin et al. |
| 2009/0180970 A1 | 7/2009 | Tamarkin et al. |
| 2009/0291917 A1 | 11/2009 | Akama et al. |
| 2009/0317338 A1 | 12/2009 | Tamarkin et al. |
| 2010/0111879 A1 | 5/2010 | Tamarkin et al. |
| 2010/0221194 A1 | 9/2010 | Loupenok |
| 2010/0266510 A1 | 10/2010 | Tamarkin et al. |
| 2011/0002857 A1 | 1/2011 | Tamarkin et al. |
| 2011/0002969 A1 | 1/2011 | Serraima et al. |
| 2011/0212033 A1 | 9/2011 | Tamarkin et al. |
| 2011/0268665 A1 | 11/2011 | Tamarkin et al. |

FOREIGN PATENT DOCUMENTS

| | | |
|---|---|---|
| CH | 639913 | 12/1983 |
| DE | 933486 | 8/1963 |
| DE | 1 882 100 | 11/1963 |
| DE | 1926796 | 11/1965 |
| DE | 4140474 | 6/1993 |
| DE | 10009233 | 8/2000 |
| DE | 10138495 | 2/2003 |
| DE | 102004016710 | 10/2005 |
| DE | 2 608 226 | 9/2007 |
| EP | 0156507 A1 | 10/1985 |
| EP | 0186453 | 7/1986 |
| EP | 211550 | 2/1987 |
| EP | 0214865 A2 | 3/1987 |
| EP | 0216856 | 4/1987 |
| EP | 0270316 | 6/1988 |
| EP | 0270316 | 8/1988 |
| EP | 297436 | 1/1989 |
| EP | 326196 | 8/1989 |
| EP | 336812 | 10/1989 |
| EP | 0391124 A2 | 10/1990 |
| EP | 0404376 | 12/1990 |
| EP | 414920 | 3/1991 |
| EP | 0484530 A1 | 5/1992 |
| EP | 485299 | 5/1992 |
| EP | 0 488 089 | 6/1992 |
| EP | 0488089 | 6/1992 |
| EP | 0488089 A1 | 6/1992 |
| EP | 504301 | 9/1992 |
| EP | 0506197 A1 | 9/1992 |
| EP | 0 528 190 | 2/1993 |
| EP | 0535327 | 4/1993 |
| EP | 0 552 612 | 7/1993 |
| EP | 0535327 | 7/1993 |
| EP | 0569773 A2 | 11/1993 |
| EP | 0598412 | 11/1993 |
| EP | 0 598 412 | 5/1994 |
| EP | 0598412 | 5/1994 |
| EP | 0598412 A2 | 5/1994 |
| EP | 0 662 431 | 7/1995 |
| EP | 0676198 | 10/1995 |
| EP | 0738516 | 10/1996 |
| EP | 0 757 959 | 2/1997 |
| EP | 0824911 | 2/1998 |
| EP | 829259 | 3/1998 |
| EP | 676198 | 10/1998 |
| EP | 928608 | 7/1999 |
| EP | 0979654 A1 | 2/2000 |
| EP | 0993827 A1 | 4/2000 |
| EP | 1025836 A1 | 8/2000 |
| EP | 1055425 A2 | 11/2000 |
| EP | 1215258 | 6/2002 |
| EP | 1 287 813 | 3/2003 |
| EP | 1287813 | 3/2003 |
| EP | 1 308 169 | 5/2003 |
| EP | 1308169 | 5/2003 |
| EP | 1 375 386 | 1/2004 |
| EP | 1 428 521 | 6/2004 |
| EP | 1428521 | 6/2004 |
| EP | 1438946 | 7/2004 |
| EP | 1189579 | 9/2004 |
| EP | 1475381 | 11/2004 |
| EP | 1483001 | 12/2004 |
| EP | 1500385 | 1/2005 |
| EP | 1 537 916 | 6/2005 |
| EP | 1600185 | 11/2005 |
| EP | 1734927 | 12/2006 |
| EP | 1758547 | 3/2007 |
| EP | 1584324 | 11/2007 |
| EP | 1889609 | 2/2008 |
| FR | 2 591 331 | 6/1987 |
| FR | 2 640 942 | 6/1990 |
| FR | 2736824 | 1/1997 |
| FR | 2774595 A | 8/1999 |
| FR | 2 789 371 | 8/2000 |

| | | | | | | |
|---|---|---|---|---|---|---|
| FR | 2 793 479 | 11/2000 | | JP | 2000191429 | 7/2000 |
| FR | 2 814 959 | 4/2002 | | JP | 2000239140 | 9/2000 |
| FR | 2 833 246 | 6/2003 | | JP | 2000351726 | 12/2000 |
| FR | 2840903 | 12/2003 | | JP | 2000354623 | 12/2000 |
| FR | 2 843 373 | 2/2004 | | JP | 2001002526 | 1/2001 |
| FR | 2 845 672 | 4/2004 | | JP | 2001019606 | 1/2001 |
| FR | 2 848 998 | 6/2004 | | JP | 2001072963 | 3/2001 |
| FR | 2860976 | 4/2005 | | JP | 2002/012513 | 1/2002 |
| FR | 2915891 | 11/2008 | | JP | 2002012513 | 1/2002 |
| GB | 808104 | 1/1959 | | JP | 2002047136 | 2/2002 |
| GB | 808105 | 1/1959 | | JP | 2002/524490 | 8/2002 |
| GB | 922930 | 4/1963 | | JP | 2002302419 | 10/2002 |
| GB | 933486 | 8/1963 | | JP | 2003/012511 | 1/2003 |
| GB | 998 490 | 7/1965 | | JP | 2003055146 | 2/2003 |
| GB | 1026831 | 4/1966 | | JP | 2004047136 A | 2/2004 |
| GB | 1033299 | 6/1966 | | JP | 2004250435 | 9/2004 |
| GB | 1081949 A | 9/1967 | | JP | 2004/348277 | 12/2004 |
| GB | 1121358 | 7/1968 | | JP | 2005314323 | 11/2005 |
| GB | 1 162 684 | 8/1969 | | JP | 2005350378 | 12/2005 |
| GB | 1170152 | 11/1969 | | JP | 2006008574 | 1/2006 |
| GB | 1 201 918 | 8/1970 | | JP | 2006/036317 | 2/2006 |
| GB | 1347950 | 2/1974 | | JP | 2006/103799 | 4/2006 |
| GB | 1 351 761 | 5/1974 | | JP | 2006525145 | 11/2006 |
| GB | 1 351 762 | 5/1974 | | JP | 2007131539 | 5/2007 |
| GB | 1 353 381 | 5/1974 | | JP | S48-92282 | 12/2007 |
| GB | 1376649 | 12/1974 | | KR | 143232 | 7/1998 |
| GB | 1397285 | 6/1975 | | KR | 2001003063 | 6/1999 |
| GB | 1408036 | 10/1975 | | RU | 2277501 | 6/2006 |
| GB | 1 457 671 | 12/1976 | | UA | 66796 | 6/2004 |
| GB | 1489672 A | 10/1977 | | WO | WO-8201821 | 6/1982 |
| GB | 2004746 A | 4/1979 | | WO | WO-86/05389 | 9/1986 |
| GB | 1561423 | 2/1980 | | WO | WO-88/01863 | 3/1988 |
| GB | 2114580 | 8/1983 | | WO | WO-8801502 | 3/1988 |
| GB | 2153686 | 8/1985 | | WO | WO-88/08316 | 11/1988 |
| GB | 2172298 | 9/1986 | | WO | WO-89/06537 | 7/1989 |
| GB | 2 206 099 | 12/1988 | | WO | WO-90/05774 | 5/1990 |
| GB | 2166651 | 5/1996 | | WO | WO 91/11991 | 8/1991 |
| GB | 2337461 | 11/1999 | | WO | WO-91/11991 | 8/1991 |
| GB | 2 367 809 | 4/2002 | | WO | WO-92/00077 | 1/1992 |
| GB | 2 406 330 | 3/2005 | | WO | 92/05763 | 4/1992 |
| GB | 2406791 | 4/2005 | | WO | WO-9205142 A1 | 4/1992 |
| IL | 49491 | 9/1979 | | WO | WO-92/11839 | 7/1992 |
| IL | 0152486 | 5/2003 | | WO | WO-9325189 | 12/1993 |
| JP | 60001113 | 4/1978 | | WO | WO-9406440 | 3/1994 |
| JP | 55069682 | 5/1980 | | WO | WO-96/03115 | 2/1996 |
| JP | 57044429 | 3/1982 | | WO | WO 96/19921 | 4/1996 |
| JP | 56039815 | 4/1984 | | WO | WO-9624325 A1 | 8/1996 |
| JP | 61275395 | 12/1986 | | WO | 96/26711 | 9/1996 |
| JP | 62241701 | 10/1987 | | WO | WO 96/27376 | 9/1996 |
| JP | 63119420 | 5/1988 | | WO | WO-96/39119 | 12/1996 |
| JP | 01100111 | 4/1989 | | WO | WO-9703638 | 2/1997 |
| JP | 01156906 | 6/1989 | | WO | WO-97/39745 | 10/1997 |
| JP | 2184614 | 7/1990 | | WO | WO-88/01863 | 3/1998 |
| JP | 2255890 | 10/1990 | | WO | WO-9817282 | 4/1998 |
| JP | 04282311 | 10/1992 | | WO | WO-98/18472 | 5/1998 |
| JP | 4312521 | 11/1992 | | WO | WO-98/19654 | 5/1998 |
| JP | 5070340 | 3/1993 | | WO | WO-98/21955 | 5/1998 |
| JP | 5213734 | 8/1993 | | WO | WO-98/23291 | 6/1998 |
| JP | 6100414 | 4/1994 | | WO | WO-98/36733 | 8/1998 |
| JP | H06-263630 | 6/1994 | | WO | 98/52536 | 11/1998 |
| JP | 6329532 | 11/1994 | | WO | WO-99/08649 | 2/1999 |
| JP | 2007/155667 | 6/1995 | | WO | WO-99/20250 | 4/1999 |
| JP | 7215835 | 8/1995 | | WO | WO-99/37282 | 7/1999 |
| JP | 8501529 | 2/1996 | | WO | WO-9953923 | 10/1999 |
| JP | 2008040899 | 2/1996 | | WO | WO-9953923 A1 | 10/1999 |
| JP | 8119831 | 5/1996 | | WO | WO-00/09082 | 2/2000 |
| JP | 8165218 | 6/1996 | | WO | WO 00/15193 | 3/2000 |
| JP | 8277209 | 10/1996 | | WO | WO-0023051 | 4/2000 |
| JP | 09 084855 | 3/1997 | | WO | WO-0033825 | 6/2000 |
| JP | 9099553 | 4/1997 | | WO | WO-0038731 | 7/2000 |
| JP | 9110636 | 4/1997 | | WO | WO-00/61076 | 10/2000 |
| JP | 10114619 | 5/1998 | | WO | WO-00/76461 | 12/2000 |
| JP | 3050289 | 9/1998 | | WO | WO-0105366 | 1/2001 |
| JP | 2010/332456 | 12/1998 | | WO | WO-01/08681 | 2/2001 |
| JP | 11501045 | 1/1999 | | WO | WO-0110961 A1 | 2/2001 |
| JP | 11250543 | 9/1999 | | WO | 01/053198 | 7/2001 |
| JP | 2000017174 A | 1/2000 | | WO | 01/054212 | 7/2001 |
| JP | 2000080017 | 3/2000 | | WO | WO-01/54679 | 8/2001 |
| JP | 2000128734 | 5/2000 | | WO | WO-0162209 A2 | 8/2001 |

| | | |
|---|---|---|
| WO | WO 01/70242 A2 | 9/2001 |
| WO | 01/82890 | 11/2001 |
| WO | WO-01/82880 | 11/2001 |
| WO | WO-0185102 A2 | 11/2001 |
| WO | WO-0185128 | 11/2001 |
| WO | WO-0195728 A1 | 12/2001 |
| WO | WO-02/00820 | 1/2002 |
| WO | WO-0215860 | 2/2002 |
| WO | WO-0215873 | 2/2002 |
| WO | WO-02/28435 | 4/2002 |
| WO | WO-02/41847 A1 | 5/2002 |
| WO | WO-02/43490 | 6/2002 |
| WO | WO-02/062324 | 8/2002 |
| WO | WO-02078667 A1 | 10/2002 |
| WO | WO-02087519 | 11/2002 |
| WO | 03/000223 | 1/2003 |
| WO | WO-03000223 A1 | 1/2003 |
| WO | WO-03002082 | 1/2003 |
| WO | 03/013984 | 2/2003 |
| WO | WO-03/051294 | 6/2003 |
| WO | WO 03/051294 | 6/2003 |
| WO | WO-03/053292 | 7/2003 |
| WO | WO-03/055445 | 7/2003 |
| WO | WO-03055454 | 7/2003 |
| WO | 03/070301 | 8/2003 |
| WO | 03/071995 | 9/2003 |
| WO | WO-03/075851 | 9/2003 |
| WO | 03/097002 | 11/2003 |
| WO | WO-03/092641 | 11/2003 |
| WO | WO-2004017962 | 3/2004 |
| WO | WO-2004/037225 | 5/2004 |
| WO | WO 2004/037225 A2 | 5/2004 |
| WO | WO-2004037197 | 5/2004 |
| WO | 2004/03284 | 8/2004 |
| WO | WO-2004/064833 | 8/2004 |
| WO | WO-2004/064833 A1 | 8/2004 |
| WO | WO-2004/071479 A1 | 8/2004 |
| WO | WO-2004064769 | 8/2004 |
| WO | WO-2004/078896 | 9/2004 |
| WO | WO-2004078158 | 9/2004 |
| WO | WO-2004093895 | 11/2004 |
| WO | WO 2004/112780 A1 | 12/2004 |
| WO | WO-2005/011567 A2 | 2/2005 |
| WO | WO-2005/018530 | 3/2005 |
| WO | WO-2005/018530 A2 | 3/2005 |
| WO | WO-2005/032522 | 4/2005 |
| WO | WO-2005/044219 | 5/2005 |
| WO | WO-2005/065652 | 7/2005 |
| WO | WO-2005063224 | 7/2005 |
| WO | WO-2005/076697 | 8/2005 |
| WO | WO-2005/097068 | 10/2005 |
| WO | WO-2005/097068 A1 | 10/2005 |
| WO | WO-2005/032522 | 11/2005 |
| WO | WO-2005/102539 | 11/2005 |
| WO | WO-2005/102539 A | 11/2005 |
| WO | WO-2005102282 A1 | 11/2005 |
| WO | WO-2005/117813 | 12/2005 |
| WO | WO-2006/003481 | 1/2006 |
| WO | WO-2006/003481 A2 | 1/2006 |
| WO | WO-2006/010589 | 2/2006 |
| WO | WO-2006011046 | 2/2006 |
| WO | WO-2006020682 A1 | 2/2006 |
| WO | WO-2006/031271 | 3/2006 |
| WO | WO-2006028339 A1 | 3/2006 |
| WO | WO-2006045170 A2 | 5/2006 |
| WO | WO-2006/091229 | 8/2006 |
| WO | WO-2006079632 A1 | 8/2006 |
| WO | WO-2006081327 | 8/2006 |
| WO | WO-2006/100485 | 9/2006 |
| WO | WO-2006/120682 | 11/2006 |
| WO | WO-2006121610 A2 | 11/2006 |
| WO | WO-2006122158 | 11/2006 |
| WO | WO-2006/129161 | 12/2006 |
| WO | WO-2006/131784 | 12/2006 |
| WO | WO-2007/007208 | 1/2007 |
| WO | WO-2007/012977 | 2/2007 |
| WO | WO-2007/023396 | 3/2007 |
| WO | WO-2007031621 A2 | 3/2007 |
| WO | WO-2007/039825 | 4/2007 |
| WO | WO-2007/050543 | 5/2007 |
| WO | WO-2007/054818 | 5/2007 |
| WO | WO-2007/072216 | 6/2007 |
| WO | WO-2007/085899 | 8/2007 |
| WO | WO-2007/085902 | 8/2007 |
| WO | WO-2007/099396 | 9/2007 |
| WO | WO-2007111962 A2 | 10/2007 |
| WO | WO-2007/039825 | 11/2007 |
| WO | WO-2008/008397 | 1/2008 |
| WO | WO-2008010963 | 1/2008 |
| WO | 2008/041045 | 4/2008 |
| WO | WO-08/38147 | 4/2008 |
| WO | WO-2008/038147 | 4/2008 |
| WO | WO-2008/075207 | 6/2008 |
| WO | WO-2008/087148 | 7/2008 |
| WO | WO-2008110872 A2 | 9/2008 |
| WO | 2008/152444 | 12/2008 |
| WO | WO-2009007785 A2 | 1/2009 |
| WO | WO-2009/069006 A2 | 6/2009 |
| WO | WO-2009/072007 A2 | 6/2009 |
| WO | WO-2009/087578 A2 | 7/2009 |
| WO | WO-2009/090495 A2 | 7/2009 |
| WO | WO-2009/090558 A2 | 7/2009 |
| WO | WO-2009/098595 A2 | 8/2009 |
| WO | WO-2011039637 | 4/2011 |
| WO | WO-2011039638 | 4/2011 |

OTHER PUBLICATIONS hydroxyethylcellulose. http://terpconnectumd.edu/~choi/MSDS/Sigma-Aldrich/HYDROXYETHYL%20CELLULOSE.pdf.*
Martindale, The extra pharmacopoeia [28th] edition, Eds.: Reynolds, J.E.F. and Prasad, A.B., The Pharmaceutical Press, London, 1982, pp. 862-864.
Tamarkin, D. et al., *Foam Carrier Containing Amphiphilic Copolymer Gelling Agent*, filed Aug. 4, 2004, U.S. Appl. No. 10/911,367.
Tamarkin, D. et al., *Foam Incorporating Eutectic Mixture*, filed Aug. 20, 2004, U.S. Appl. No. 10/922,555.
Tamarkin, D., et al. *Oleaginous Pharmaceutical and Cosmetic Foam*, filed Apr. 28, 2004, U.S. Appl. No. 10/835,505.
Tamarkin, D., et al. *Penetrating Pharmaceutical Foam*, filed Aug. 20, 2004, U.S. Appl. No. 10/922,358.
Wormser et al. Arch. Toxicol., 1997, 71, 165-170.
Wormser et al. *Letters to the Editor*, Burns, 1998, 24, 383.
Barry, B.W. et al, Comparative bio-availability and activity of proprietary topical corticosteroid preparations: vasoconstrictor assays on thirty-one ointments, British Journal of Dermatology, 93, 563-571, 1975.
Tamarkin, D., et al. Body Cavity Foam, U.S. Appl. No. 11/116,761, filed Apr. 28, 2005.
Tamarkin, D., et al. Nonsteroidal Immunomodulating Kit and Composition and Uses Thereof, U.S. Appl. No. 11/078,902, filed Mar. 11, 2005.
Tamarkin, D., et al. Steroid Kit and Foamable Composition and Uses, U.S. Appl. No. 11/114,410, filed Apr. 26, 2005.
Tamarkin, D., et al. Vasoactive Kit and Composition and Uses Thereof, U.S. Appl. No. 11/124,676, filed May 9, 2005.
Alcohol SDA 40B.http://www.pharmco-prod.com/pages/MSDS/SDA_40B_200.pdf Accessed Dec. 9, 2008, 2 pages.
Ambrose, Ursual et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, vol. 35, No. 9, pp. 1799-1803, 1991.
Arisan, http://www.arisankimya.com/kozmetik.htm Accessed Dec. 10, 2008.
Benet, et al., App-lication of NMR for the Determination of HLB Values of Nonionic Surfactants, Journal of the American Oil Chemists Society, vol. 49, 1972, 499-500.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Carbowax 1000MSDS; http://www.sciencelab.com/xMSDS-Polyethylene_glycol_1000-9926622. Accessed Dec. 13, 2008, 6 pages.

Cheshire, et al., Disorders of Sweating, www.medscape.com, Semin Neurol 23(4):399-406, 2003.
Coetzee, "Acceptability and Feasibility of Micralax applicators and of methyl cellulose gel placebo for large-scale clinical trials of vaginal microbicides," Nicol.AIDS 2001, vol. 15, No. 14, pp. 1837-1842.
D.W.A. Sharp Dictionary of Chemistry, Penguin Books, 1983, 3 pages.
Dalby, "Determination of Drug Solubility in Aerosol Propellants," Pharmaceutical Research, vol. 8, No. 9, 1991, pp. 1206-1209.
Denatonium Benzoate http://www.newdruginfo.com/pharmaceopeia/usp28/v28230/usp28nf23s0__m22790.htm Accessed Dec. 9, 2008.
Emulsifiers with HLB values. http://www.theherbarie.com/files/resources-center/formulating/Emulsifiers_HLB_Values.pdf accessed Aug. 5, 2009.
Ethanol, Accessed http://www.sigmaaldrich.com/catalog/ProductDetail.do?N4=E7023SIAL&N5=SEARCH_CONCAT_PNOBRAND_KEY&F=SPEC Dec. 9, 2008, 2 pages.
European Patent Application No. 06831721, Official Action, Feb. 3, 2009, 9 pages.
Flick, Cosmetic and Toiletry Formulations, vol. 5, 2nd Edition, Copyright 1996.
Fontana, Anthony, J., "Water Activity: Why it is Important for Food Safety," International Conference on Food Safety, Nov. 16-18, 1998, 9 pages.
Friedman et al., Antibiotic Kit and Composition and Uses Thereof, filed Jun. 7, 2006, U.S. Appl. No. 11/448,490.
Gill, A.M, et al., "Adverse Drug Reactions in a Paediatric Intensitve Care Unit," Acta Paediatr 84:438-441, 1995.
Hall, Karla, "Diaper Area Hemanglomas: A Unique Set of Concerns," http://members.tripod.com/~Michelle_G/diaper.html, Dec. 1, 2008, 8 pages.
Hashim, et al. "Tinea versicolor and visceral leishmaniasis," Int J Dermatol., Apr. 1994; 33(4), pp. 258-259 (abstract only).
Hepburn, NC., "Cutaneous leishmaniasis," Clin Exp Dermatol, Jul. 2000; 25(5), pp. 363-70 (abstract only).
Hill, Randall M. (Ed.) Silicone Surfactants, Table of Contents and Chapter 7, "Silicone Surfactants: Applicants in the Personal Care Industry," by David T. Floyd (30 pages).
Innocenzi, Daniele et al., "An Open-Label Tolerability and Effacy Study of an Aluminum Sesquichlorhydrate Topical Foam in Axillary and Palmar Primary Hyperhidrosis," Dermatologic Therapy, vol. 21, S27-S30, 2008.
International Search Report and Written Opinion, International Application No. PCT/IB2006/003628, Foamix Ltd., Dec. 7, 2007, 15 pages.
International Search Report and Written Opinion, International Application No. PCT/US2007/004459, Foamix Ltd., Dec. 9, 2008, 2 pages.
International Search Report for International Application No. PCT/IB2006/003974, Feb. 25, 2008 (3 pages).
International Search Report, International Patent Application No. PCT/IB2007/003463, Foamix, Ltd., Jul. 18, 2008, 3 pages.
International Search Report, International Patent Application No. PCT/IB2007/003759, Foamix Ltd., Jul. 8, 2008 (3 pages).
Kalkan, et al., The Measurement of Sweat Intensity Using a New Technique, Tr. J. of Medical Sciences 28, 515-517 (1998).
Kathon™ CG (product information sheet by Rohm and Haas, Jun. 2006).
Kinnunen, Contact Dermatitis Sep. 1989; 21(3): 154-8.
Koerber, S., "Humectants and Water Activity," Water Activity News, 2000, ISSN No. 1083-3943.
Licking Vaginal Dryness without a Prescription. Accessed http://www.estronaut.com/a/vag_dryness.htm on Dec. 14, 2008.
Merriam-Webster Online Dictionaary, 2008, "Mousse," Merriam-Webster Online, Dec. 8, 2008 http://www.merriam-webster.com/dictionary/mousse.
Metronidazole. www.usp.org/pdf/EN/veterinary/metronidazole.pdf. accessed Sep. 10, 2009, 4 pages.
Morgan, Timothy M., et al., "Enhanced Skin Permeation of Sex Hormones with Novel Topical Spray Vehicles," Journal of Pharmaceutical Sciences, vol. 87, No. 10, Oct. 1998, pp. 1213-1218.
Office Action received from the U.S. Patent Office for U.S. Appl. No. 11/430,437, May 9, 2008, 55 pages.
Office Action received from the U.S. Patent Office, U.S. Appl. No. 11/430,599, Jul. 28, 2008, 58 pages.
OM Cinnamate. http://www.makingcosmetics.com/sunscreens/OM-Cinnamate-p102.html accessed Sep. 26, 2009.
Pendergrass, Gynecol Obstet. Invest. 1996:42(3):178-82.
Progesterone MSDS. http://www.usp.org.pdf.EN/referenceStandards/msds/1568007.pdf on Dec. 14, 2002, 5 pages.
Savin, et al., "Tinea versicolor treated with terbinafine 1% solution," Int J. Dermatol, Nov. 1999; 38(11), pp. 863-865.
Schmidt A., "Malassezia furfur: a fungus belonging to the physiological skin flora and its relevance in skin disorders," Curtis., Jan. 1997; 59(1), pp. 21-24 (abstract).
Scott as Published in Pharmaceutical Dosage Forms; Disperse Systems, vol. 3, Copyright 1998.
Shear, et al., "Pharmacoeconomic analysis of topical treatments for tinea infections," Pharmacoeconomics. Mar. 1995; 7(3); pp. 251-252 (abstract only).
Sigma Aldrich, "HLB-Numbers in Lithography Nanopatterning," http://www.sigmaaldrich.com/materials-science/micro-and-nanoelectronics/lithography-nanopatterning/hlb-numbers.html, accessed: Feb. 2, 2009, pp. 1-3.
Sigma-Aldrich, Material Safety Data Sheet, Hydroxyethyl Cellulose, Mar. 3, 2004, 5 pages.
Skin Biology, CP Serum—Copper-Peptide Serum for Skin Regeneration and Reducing Wrinkles, Skin Biology, http://web.archive.org/web/20030810230608/http://www.skinbio.com/cpserum.html, Dec. 1, 2008, 21 pages.
Squire. J, Dermatolog Treat. Jun. 2002;13(2):51-60.
Tan et al., "Effect of Carbopol and Polyvinylpyrrolidone on the Mechanical, Rheological, and Release Properties of Bioadhesive Polyethylene Glycol Gels," AAPS PharmSciTech, 2000; 1 (3) article 24 (2000), 10 pages.
Torres-Ridriguez, JM., "New topical antifungal drugs," Arch Med Res. 1993 Winter; 24(4), pp. 371-372 (abstract).
Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid-=0709F73D-A849-80CA-5FB784E866B576D1. Accessed Dec. 9, 2008.
International Search Report, International Patent Application No. PCT/IB2007/003759, Foamix Ltd., Jul. 8, 2008 (2 pages).
"Licking Vaginal Dryness Without a Prescription," Estronaut, Dec. 14, 2008, 3 pages.
Bucks, Daniel A.W., et al., "Bioavailability of Topically Administered Steroids: A 'Mass Balance' Technique," Journal of Investigative Dermatology, vol. 91, No. 1, Jul. 1988, pp. 29-33.
Gill, A.M, et al., "Adverse Drug Reactions in a Paediatric Intensitve Care Unit," Acta Paediatr 84:438-441, 1995.
Gschnait, F., et al., "Topical Indomethacin Protects from UVB and UVA Irradiation," Arch. Dermatol. Res. 276:131-132, 1984.
Hall, Karla, "Diaper Area Hemangiomas: A Unique Set of Concerns," http://members.tripod.com/~Michelle_G/diaper.html, Dec. 1, 2008, 8 pages.
Galligan, John et al., "Adhesive Polyurethane Liners for Anterior Restorations," J. Dent. Res., Jul.-Aug. 1968, pp. 629-632.
Innocenzi, Daniele et al., "An Open-Label Tolerability and Effiacy Study of an Aluminum Sesquichlorhydrate Topical Foam in Axilliary and Palmar Primary Hyperhidrosis," Dermatologic Therapy, vol. 21, S27-S30, 2008.
Coetzee, Nicol et al., "Acceptability and Feasibility of Micralax Applicators and of methyl Cellulose Gel Placebo for Large-Scale Clinical Trials of Vaginal Microbicides," Concise Communication, 2001, vol. 15, No. 14, pp. 1837-1842.
Pendergrass, P.B. et al., "The Shape and Dimension of the Human Vagina as Seen in Three-Dimensional Vinyl Polysiloxane Casts," Gynecol Obstet. Invest. 1996:42(3), 2 pages.
Merriam-Webster Online Dictionary, 2008, "Mousse," Merriam-Webster Online, Dec. 8, 2008 http://www.merriam-webster.com/dictionary/mousse.
Abstract for TR-436-t-Butyl Alcohol, National Toxicology Program, Toxicology and Carcinogenesis Studies of t-Butyl Alcohol (CAS No. 75-65-0) in F344/N Rats and B6C3F1 Mice (Drinking Water Studies), http://ntp.niehs.nih.gob/?objectid=0709F73D-A849-80CA-5H:3784E8668576D1. Accessed Dec. 9, 2008, 4 pages.
Denatonium Benzoate, Chemical Structure Molecular Form Reference Standard, http://www.newdruginfo.com/pharmaceopeia/usp28/v28230/usp28nf23s0_m22790.htm Accessed Dec. 9, 2008, 2 pages.
Scott, Roy R., as Published in Pharmaceutical Dosage Forms; Disperse Systems, vol. 3, Copyright 1998, 120 pages.
Flick, Cosmetic and Toiletry Formulations, vol. 5, 2nd Edition, Copyright 1996, (259-309), 63 pages.
Arisan, 8 pages, http://www.arisankimya.com/kozmetik.htm Accessed Dec. 10, 2008.
Sigma-Aldrich, Ethanol, E7023 Ethanol 200 Proof (Absolute) for Molecular Biology, 2 pages http://www.sigmaaldrich.com/catalog/ProductDetail.do?N4=E7023SIAL&N5=SEARCH_CONCAT_PNOBRAND_KEY&F=SPEC Accessed Dec. 9, 2008.
Material Safety Data Sheet, Alcohol SDA 40B.http://www.pharmco-prod.com/pages/MSDS/SDA_40B_200.pdf Pharmco-AAPER, Dec. 2005, 2 ages Accessed Dec. 9, 2008.
Kinnuen, T., et al., "Skin Reactions to Hexylene Glycol," Contact Dermatitis, Sep. 21, 1989, 2 pages.
Material Safety Data Sheet, Polyethylene Glycol 1000 MSDS, ScienceLab.com, Oct. 10, 2005, 6 pages.
"HLB Systems", http://pharmcal.tripod.com/ch17.htm, Accessed Sep. 17, 2010, pp. 1-3.
Adachi, Shuji. "Storage and Oxidative Stability of O/W/ Nano-emulsions." Foods Food Ingredients. J. Jpn. vol. 209, No. 11. 2004. 1 page.
Anton, N. et al. "Water-in-Oil Nano-Emulsion Formation by the phase inversion Temperature Method: A Novel and General Concept, a New Template for Nanoencapsulation." University of Angers. Paris, France. No Date Listed. 2 pages.
Arct, et al., "Common Cosmetic Hydrophilic Ingredients as Penetration Modifiers of Flavonoids", International Journal of Cosmetic Science, 24(6):357-366 (2002)—Abstract, 1 page.
Augsburger, Larry L. et al. "Bubble Size Analysis of High Consistency Aerosol Foams and Its Relationship to Foam Rheology. Effects of Container Emptying, Propellent Type, and Time." Journal of Pharmaceutical Sciences. vol. 57, No. 4. Apr. 1968. pp. 624-631.
Austria, et al., "Stability of Vitamin C Derivatives in Solution and Topical Formulations", Journal of Pharmaceutical and Biomedical Analysis, 15:795-801 (1997).
Bernstein, et al., Effects of the Immunomodulating Agent R837 on Acute and Latent Herpes Simplex Virus Type 2 Invections, Antimicrobial Agents and Chemotherapy, 33(9):1511-1515 (1989).
Blute, "Phase behavior of alkyl glycerol ether surfactants", Physical Chemistry Tenside Sur. Det., 35(3):207-212 (1998).
Brenes, et al., "Stability of Copigmented Anthocyanins and Asorbics Acid in a Grape Juice Model System", J. Agric Food Chem, 53(1):49-56 (2005)—Abstrace, 1 page.
Bronopol. Revtrieved online on Jun. 4, 2011. <URL:http://chemicalland21.com/specialtychem/perchem/BRONOPOL.html>. Jul. 17, 2006. 4 pages.
Buck, et al., "Treatment of Vaginal Intraephithelial Neoplasia (Primarily Low Grade) with Imiquimod 5% Cream", Journal of Lower Genetial Tract Disease, 7(3):290-293 (2003).
Bunker, et al., "Alterations in Scalp Blood Flow after the Epicutaneous Application of 3% Minoxidil and 0.1% Hexyl Nicotinate in Alopecia", Presented as a poster at the meeting of the British Society for Investigavie Dermatology, York, Sep. 1986 (2 pages).
Burton, et al., "Hypertrichosis Due to Minoxidil", British Journal of Dermatology, 101:593-595 (1979).
Campos, et al., "Ascorbic Acid and Its Derivatives in Cosmetic Formulations", Cosmetics and Toiletries, 115(6):59-62 (2000)—Abstract, 1 page.
Carelli, et al., "Effect of Vehicles on Yohimbine Permeation Across Excised Hairless Mouse Skin", Pharm Acta Helv, 73(3):127-134 (1998)—Abstract, 1 page.
Chebil, et al., "Soulbility of Flavonoids in Organic Solvents", J. Chem. Eng. Data, 52(5):1552-1556 (2007)—Abstract, 1 page.
Chevrant-Breton, et al., "Etude du Traitement Capillaire <<Bioscalin>> dans les Alopecies Diffuses de la Femme", Gazette Medicale, 93(17):75-79 (1986).

Chiang, et al., "Bioavailability Assessment of Topical Delivery Systems: In Vitro Delivery of Minoxidil from Prototypical Semi-Solid Formulations", Int. J. Pharm, 49(2):109-114 (1989)—Abstract, 1 page.
Chinnian, et al., "Photostability Profiles of Minoxidil Solutions", PDA J. Pharm Sci Technol., 50(2):94-98 (1996)—Abstract, 1 page.
Chollet, et al., "Development of a Topically Active Imiquimod Formulation", Pharmaceutical Development and Technology, 4(1):35-43 (1999).
Chollet, et al., "The Effect of Temperatures on the Solubility of Immiquimod in Isostearic Acid", Abstract 3031, Pharmaceutical Research, vol. 14, No. 11 Supplemental (Nov.), p. S475 (1997), 2 pages.
Colloidal Silica. Retrieved online on Jun. 4, 2011. <URL:http://www.grace.com/engineeredmaterials/materialsciences/colloidalsilica/default.aspx>. Copyright 2011. 4 pages.
Croda 2. Croda Cetomacrogol 1000 Product Information Sheet. 2011 (no month given). 1 page.
Croda. Aracel 165 Product Summary. 2011 (no month given). 1 page.
Dawber, et al., "Hypertrichosis in Females Applying Minoxidil Topical Solution and in Normal Controls", JEADV, 17:271-275 (2003).
Dentinger, et al., "Stability of Nifedipine in an Extemporaneously Compounded Oral Solution", American Journal of Health-System Pharmacy, 60(10):1019-1022 (2003)—Abstract, 1 page.
disorder. (2007). In the American Heritage Dictionary of the English Language. Retrieved from http://www.credoreference.com/entry/hmdictenglang/disorder. 1 page.
Draelos, Z. D. "Antiperspirants and the Hyperhidrosis Patients." Dermatologic Therapy. 2001. vol. 14. pp. 220-224.
Edens, et al., "Storage Stability and Safey of Active Vitamin C in a New Dual-Chamber Dispenser", Journal of Applied Cosmetology, 17(4):136-143 (1999)—Abstract, 1 page.
Edirisinghe, et al., "Effect of fatty acids on endothelium-dependent relaxation in the rabbit aorta", Clin Sci (Lond). Aug. 2006; 111(2): 145-51.
Edwards, "Imiquimod in Clinical Practice", J. Am Acad Dermatol., 43(1, Pt 2):S12-S17 (2000)—Abstract, 1 page.
Encyclopedia of Pharmaceutical Technology, Second Edition, vol. 3, Copyright 2002, 4 pages.
English machine translation of JP-08165218 (1996)—9 pages.
English translation of abstract for Japanese Patent Publication No. 4892282 (1992)—1 page.
Esposito, E. et al. "Nanosystems for Skin Hydration: A Comparative Study." International Journal of Cosmetic Science. 29. 2007. pp. 39-47.
Ethylene Oxide Derivatives: An Essence of Every Industry. A definition of Emulsifier. Http://www.emulsifiers.in/ethylene_oxide_derivatives2.htm. Accessed Jul. 12, 2011. 3 pages.
Farahmand, et al., "Formulation and Evaluation of a Vitamin C Multiple Emulsion", Pharmaceutical Development and Technology, 11(2):255-261 (2006)—Abstract, 1 page.
Final Office Action for U.S. Appl. No. 11/430,437, Tamarkin et al., Dec. 16, 2008, 24 pages.
Gallarate, et al., "On the Stability of Ascorbic Acid in Emulsified Systems for Topical and Cosmetic Use", International Journal of Pharmaceutics, 188:233-241 (1999).
Gelbard et al. "Primary Pediatric Hyperhidrosis: A Review of Current Treatment Options." Pediatric Dermatology. 2008. 25 (6). pp. 591-598.
Gladkikh, "Ascorbic Acid and Methods of Increasing its Stability in Drugs", Translated from Khimiko-Farmatsevticheskii Zhurnal, 4(12):37-42 (1970)—1 page.
Graves, S. et al. "Structure of Concentrated Nanoemulsions." The Journal of Chemical Physics.. 122 America Institute of Physics. Published Apr. 1, 2005. 6 pages.
Hallstar. Retrieved online on Jun. 4, 2011. <URL:http://www.hallstar.com/pis.php?product=1H022>. 1 page.
Harrison, et al., "Effects of cytokines and R-837, a cytokine inducer, on UV-irradiation augmented recurrent genital herpes in guinea pigs", Antivial Res., 15(4):315-322 (1991).
Harrison, et al., "Modification of Immunological Responses and Clinical Disease During Topical R-837 Treatment of Genital HSV-2 Infection", Antiviral Research, 10:209-224 (1988).

Harrison, et al., "Pharmacokinetics and Safety of Iminquimod 5% Cream in the Treatment of Actinic Keratoses of the Face, Scalp, or Hands and Arms", Arch. Dermatol. Res., 296(1):6-11 (2004)—Abstract, 1 page.
Heart Failure, The Merck Manual, 2008 <<http://www.merck.com/mmhe/sec03/ch025/ch025a.html>> 12 pages.
http://ibabydoc.com/online/diseaseeczema.asp., Atopic Dermatitis, Copyright 2000, 6 pages.
http://web.archive.org/web/20000106225413/http://pharmacy.wilkes.edu/kibbeweb/lab7.html, Characteristics of Surfactants and Emulsions, Jan. 29, 2010, 5 pages.
http://www.agworkshop.com/p3.asp, AG&Co. Essential oil workshop. 1 page. Accessed Jan. 31, 2010.
ICI Americas Inc. "The HLB System: A Time-Saving Guide to Emulsifier Selection." Mar. 1980. pp. 1-22.
Hubbe, Martin. Mini-Encyclopedia of Papermaking Wet-End Chemistry: Additives and Ingredients, their Composition, Functions, Strategies for Use. Retrieved online on Jun. 4, 2011. <URL://http://www4.ncsu.edu/~hubbe/CSIL.htm>. Feb. 1, 2001. 2 pages.
Ikuta, et al., "Scanning Electron Microscopic Observation of Oil/Wax/Water/Surfacant System", Journal of SCCJ, 34(4):280-291 (2004)—Abstract, 1 page.
Indomethacin. Retrieved online on Jun. 3, 2011. <URL:http://it03.net/com/oxymatrine/down/1249534834.pdf>. Aug. 15, 2009. 3 pages.
International Search Report and Written Opinion for International Application No. PCT/IB10/02241 mailed Feb. 10, 2011. 9 pages.
International Search Report and Written Opinion for International Application No. PCT/IB10/02613 mailed Mar. 16, 2011. 9 pages.
International Search Report and Written Opinion for International Application No. PCT/IB10/02617 mailed Mar. 15, 2011. 10 pages.
International Search Report and Written Opinion, International Patent Application No. PCT/IB2006/004026, Foamix, Ltd., Jun. 20, 17 pages.
Invitation to Pay Additional Fees for International Application No. PCT/IB2009/005012 mailed Jul. 27, 2010. 13 pages.
Izquierdo, P. et al. "Formation and Stability of Nano-Emulsions Prepared Using the Phase Inversion Temperature Method." University of Barcelona. Sep. 17, 2001. 1 page.
Kanamoto, et al., "Pharmacokinetics of two rectal dosage forms of ketoprofen in patients after anal surgery," J Pharmacobiodyn., Mar. 1988; 11(3):141-5.
Kang, et al., "Enhancement of the Stability and Skin Penetration of Vitamin C by Polyphenol", Immune Netw., 4(4):250-254 (2004)—Abstract, 1 page.
Karasu, T.B. et al., "Treatment of Patients with Major Depressive Disorder, Second Edition," pp. 1-78, 2000.
Kim, "Stability of Minoxidil in Aqueous Solution", Yakhak Hoechi, 30(5):228-231 (1986)—Abstract, 1 page.
Kleber, M.D., H.D. et al., "Treatment of Patients with Substance Use Disorders, Second Edition," pp. 1-276, 2006.
Kreuter, J. "Nanoparticles and microparticles for drug and vaccine delivery," J. Anat. (1996) 189, pp. 503-505.
Kumar, J. et ak., "Application of Broad Spectrum Antiseptic Povidone Iodine as Powerful Action: A Review," Journal of Pharmaceutical Science and Technology vol. 1(2), 2009, 48-58.
Kwak et al. "Study of Complete Transparent Nano-Emulsions which Contain Oils." IFSCC Conference 2003, Seoul, Korea, Sep. 22-24, 2003. 3 pages.
Lautenschlager, Dr. Hans. "A Closer Look on Natural Agents: Facts and Future Aspects." Kosmetic Konzept. Kosmetische Praxis. 2006 (no month given). (5), 8-10. 3 pages.
Lebwohl et al. "Treatment of Psoriasis. Part 1. Topical Therapy and Phototherapy." *J. Am. Acad. Dermatol.* 45:487-498. Oct. 2001.
Lee, et al., "The Stabilization of L-Ascorbic Acid in Aqueous Solution and Water-in-Oil-in-Water Double Emulsion by Controlling pH and Electrolyte Concentration", J. Cosmet. Sci., 55:1-12 (Jan./Feb. 2004).
Leung, et al., "Bioadhesive Drug Delivery in Water-Soluble Polymers," American Chemical Society, Chapter 23, 1991, pp. 350-366.
Lippacher, A. et al. "Liquid and Semisolid SLN Dispersions for Topical Application Rheological Characterization." European Journal of Pharmaceutics and Biopharmaceutics. 58. 2004. pp. 561-567.

Lupo, "Antioxidants and Vitamins in Cosmetics", Clinics in Dermatology, 19:467-473 (2001).
Merck Manual Home Edition. "Excessive Sweating: Sweating Disorders." Accessed Apr. 14, 2011 at www.merckmanuals.com/home/print/sec18/ch206/ch206c.html. 2 pages.
Merck Index, An Encyclopedia of Chemicals, Drugs, and Biologicals. $13^{th}$ Edition. O'Neil et al eds. Entries 1058, 2350, 6143, and 8803. 2001. 7 pages.
Messenger, et al., "Minoxidil: Mechanisms of Action on Hair Growth", British Journal of Dermatology, 150:186-194 (2004).
Metz, et al., "A Phase I Study of Topical Tempol for the Prevention of Alopecia Induced by Whole Brain Radiotherapy", Clinical Cancer Research, 10:6411-6417 (2004).
Meucci, et al., "Ascorbic Acid Stability in Aqueous Solutions", Acta Vitaminol Enzymol, 7(3-4):147-153 (1985)—Abstract, 1 page.
MMP Inc. International Development and Manufacturing, "Formulating specialities," http://mmpinc.com, 3 pages. Feb. 2, 2010.
Molan, Peter Clark, "World Wide Wounds," Dec. 2001, 13 pages.
No Author Listed. "Opitmization of Nano-Emulsions Production by Microfluidization." European Food Research and Technology. vol. 225, No. 5-6. Sep. 2007. Abstract. 1 page.
Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).
Paula. http://ww.cosmeticscop.com/cosmetic-ingredient-dictionary/definition/259/c12-15-alkyl-benzoate.aspx. Printed Oct. 24, 2010. 1 page.
PCT Search Report and Written Opinion for International Application No. PCT/IB2010/001126 mailed Apr. 20, 2011, 12 pages.
prevent. (2007). In the American Heritage Dictionary of the English Language. Retrieved from http://www.credoreference.com/entry/hmdictenglang/prevent. 1 page.
Psoriasis, http://www.quickcare.org/skin/causes-of0psoriasis.html. Accessed Sep. 9, 2010—3 pages.
Purcell, Hal C. "Natural Jojoba Oil Versus Dryness and Free Radicals." Cosmetics and Toiletries Manufacture Worldwide. 1988. 4 pages.
Raschke, et al., "Topical Activity of Ascorbic Acid: From in Vitro Optimization to in Vivo Efficacy", Skin Pharmacology and Physiology, 17(4):200-206 (2004)—Abstract, 1 page.
Receptacle. Merriam Webster. Http://www.merriam-webster.com/dictionary/receptacle. Accessed Jul. 12, 2011. 1 page.
Richwald, "Imiquimod", Drugs Today, 35(7):497 (1999)—Abstract, 1 page.
Rieger and Rhein. "Emulsifier Selection/HLB." Surfactants in Cosmetics. 1997 (no month given). 1 page.
Schutze, M.D., Harry "Iodine and Sodium Hypochlorite as Wound Disinfectants," The British Medical Journal, pp. 921-922, 1915.
Scientific Discussion for the approval of Aldara, EMEA 2005 (10 pages.).
Seborrheic Dermatitis, http://www.cumc.columbia.edu/student/health/pdf/R-S/Seborrhea%20Dermatitis.pdf. Access Sep. 9, 2010, 2 pages.
Sheu, et al., "Effect of Tocopheryl Polyethylene Glycol Succinate on the Percutaneous Penetration of Minoxidil from Water/Ethanol/Polyethylene Glycol 400 Solutions", Drug Dev. Ind. Pharm., 32(5):595-607 (2006)—Abstract, 1 page.
Shim, et al., "Transdermal Delivery of Mixnoxidil with Block Copolymer Nanoparticles", J. Control Release, 97(3):477-484 (2004)—Abstract, 1 page.
Silicone. Definition. Retrieved Apr. 19, 2011 from http://www.oxforddictionaries.com/definition/silicone?view=uk. 1 page.
Simovic, S. et al., "The influence of Processing Variables on Performance of O/W Emulsion Gels Based on Polymeric Emulsifier (Pemulen OTR-2NF)," International Journal of Cosmetic Science, vol. 2(2): abstract only. Dec. 24, 2001, 1 page.
Skin Deep Cosmetics. PPG-40-PEG-60 Lanolin Oil http://www.cosmeticsdatabase.com/ingredient/722972/PPG-40-PEG-60_Lanolin_Oil/?ingred06=722972. 3pages.
Sonneville-Aubrun, O. et al. "Nanoemulsions: A New Vehicle for Skincare Products." Advances in Colloid and Interface Science. 108-109.. 2004. pp. 145-149.

Sreenivasa, et al., "Preparation and Evaluation of Minoxidil Gels for Topical Application in Alopecia", Indian Journal of Pharmaceutical Sciences, 68(4):432-436 (2006), 11 pages.

Stehle, et al., "Uptake of Minoxidil from a New Foam Formulation Devoid of Propylene Glycol to Hamster Ear Hair Follicles", Abstract 606, 1 page.

Sugisaka, et al., "The Physiochemical Properties of Imiquimod, The First Imidazoquinoline Immune Response Modifier", Abstract 3030, Pharmaceutical Research, vol. 14, No. 11 Supplemental (Nov.), p. S475 (1997), 2 pages.

Surfactant. Wikipedia—http://en.wikipedia.org/wiki/surfactant. Printed Oct. 24, 2010. 1 page.

Sweetman, Sean C. Martindale: The Complete Drug Reference. 33rd Edition. London. Pharmaceutical Press. Jun. 21, 2002. pp. 1073 and 1473. 5 pages.

Tanhehco, "Potassium Channel Modulators as Anti-Inflammatory Agents", Expert Opinion on Therapeutic Patents, 11(7):1137-1145 (2001)—Abstract, 3 pages.

Tarumoto, et al., Studies on toxicity of hydrocortisone 17-butyrate 21-propionate -1. Accute toxicity of hydrocortisone 17-butyrate 21-propionate and its analogues in mice, rats and dogs (authors trans), J Toxicol Sci., Jul. 1981; 6 Suppl: 1-16.

Tata, et al., "Penetration of Minoxidil from Ethanol Propylene Glycol Solutions: Effect of Application Volume on Occlusion", Journal of Pharmaceutical Sciences, 84(6):688-691 (1995).

Trofatter, "imiquimod in clinical Practice", European Journal of Dermatology, 8(7 Supp.):17-19 (1998)—Abstract, 1 page.

Tsai, et al., "Drug and Vehicle Deposition from Topical Applications: Use of in Vitro Mass Balance Technique with Minosidil Solutions", J. Pharm. Sci., 81(8):736-743 (1992)—Abstract, 1 page.

Tsai, et al., "Influence of Application Time and Formulation Reapplication on the Delivery of Minoxidil through Hairless Mouse Skin as Measured in Franz Diffusion Cells", Skin Pharmacol., 7:270-277 (1994).

Tyring, "Immune-Response Modifiers: A New Paradigm in the Treatment of Human Papillomavirus", Current Therapeutic Research, 61(9):584-596 (2000)—Abstract, 1 page.

Uner, M. et al. "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel." Pharmazie. 60. 2005. 5 pages.

Veron, et al., "Stability of Minoxidil Topical Formulations", Ciencia Pharmaceutica, 2(6):411-414 (1992), Abstract, 1 page.

Williams, "Scale up of an olive/water cream containing 40% diethylene glycol momoethyl ether", Dev. Ind. Pharm., 26(1):71-77 (2000).

U.S. Appl. No. 60/789,186, Apr. 4, 2006, Tamarkin.
U.S. Appl. No. 60/815,948, Jun. 23, 2006, Tamarkin.
U.S. Appl. No. 60/818,634, Jul. 5, 2006, Friedman.
U.S. Appl. No. 60/843,140, Sep. 8, 2006, Tamarkin.
U.S. Appl. No. 61/248,144, Oct. 2, 2009, Tamarkin.
U.S. Appl. No. 61/322,148, Apr. 8, 2010, Tamarkin.
U.S. Appl. No. 61/363,577, Jul. 12, 2010, Eini.

Gill, A.M, et al., "Adverse Drug Reactions in a Paediatric Intensive Care Unit," Acta Paediatr 84:438-441, 1995.

Gladkikh, "Ascorbic Acid and Methods of Increasing its Stability in Drugs", Translated from Khimilo-Farmatsevticheskii Zhurnal, 4(12):37-42 (1970)—1 page.

Glaser, et al., Hyperhidrosis: A Comprehensive and Practical Approach to Patient Management, Expert Rev. Dermatol. 1(6), 773-775 (2006).

Groveman, et al., "Lack of Efficacy of Polysorbate 60 in the Treatment of Male Pattern Baldness", Arch Intern Med, 145:1454-1458 (1985).

Gschnait, F., et al., "Topical Indomethacin Protects from UVB and UVA Irriadiation," Arch. Dermatol. Res. 276:131-132, 1984.

Hakan, et al., "The protective effect of fish oil enema in acetic acid and ethanol induced colitis," The Turkish Journal of Gasroenterology, 2000, vol. 11, No. 2, pp. 155-161.

Harrison, et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, 38(9):2059-2064 (1994).

Li, et al., "Solubility Behavior of Imiquimod in Alkanoic Acids", Abstract 3029, Pharmaceutical Research, vol. 14, No. 11 Supplemental (Nov.), p. S475 (1997), 2 pages.

Material Safety Data Sheet, Progesterone, Apr. 26, 2006, 5 pages.

Merck index, 10th edition, Merck & Co., Inc.: Rahway, NJ, 1983, pp. 39 (entry 242 for allantoin).

Merriam Webster Online Dictionary [online] retrieved from http://www.merriam-webster.com/cgi-bin/dictionary?book=dictionary&va=derivative on Jul. 5, 2008; 1 page.

Merriam-Webster Online Dictionaary, 2008, "Mousse," Merriam-Webster Online, Dec. 8, 2008 http://www.merriam-webster.com/dictionary/mousse, 2 pages.

Olsen, et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, 57:767-774 (2007).

OM Cinnamate. http://www.makingcosmetics.com/sunscreens/OM-Cinnamate-p102.html accessed Sep. 26, 2009, 1 page.

Padhi et al., "Phospho-olicines as positive-electrode materials for rechargeable lithium batteries," J. Electrochemical Soc., 1997, 144(4): 1188-1194.

Pakpayat, et al., "Formulation of Ascorbic Acid Microemulstions with Alkyl Polyglycosides", European Journal of Pharmaceutics and Biopharmaceutics, 72:444-452 (2009).

Pendergrass, "The shape and dimension of the human vagina as seen in three-dimensional vinyl polysiloxane casts," Gynecol Obstet. Invest. 1996:42(3):178-82.

Prescription Information for Aldara, Mar. 2007 (29 pages).

Ravet et al., "Electroactivity of natural and synthetic triphylite," J. of Power Sources, 2001, 97-98: 503-507.

Raymond, Iodine as an Aerial Disinfectant, Journal of Hygiene, vol. 44, No. 5 (May 1946), pp. 359-361.

Rosacea, http://clinuvel.com/skin-conditions/common-skin-conditions/rosacea#h0-6-prevention. Accessed Sep. 9, 2010, 5 pages.

Schmidt A., "Malassezia furfur: a fungus belonging to the physiological skin flora and its relevance in skin disorders," Curtis., Jan. 1997; 59(1), pp. 21-4 (abstract).

Shrestha et al., Forming properties of monoglycerol fatty acid esters in nonpolar oil systems, Langmuir, 2006, 22: 8337-8345.

Stehle et al., Uptake of minoxidil from a new foam formulation devoid of propylene glycol to hamster ear hair follicles, J. Invest. Dermatol., 2005, 124(4), A101.

Sweetman, Sean C. Martindale: The Complete Drug Reference. 33rd Edition. London. Pharmaceutical Press. Jun. 21, 2002. pags. 1073 and 1473. 5 pages.

Tadros, Tharwat F. "Surfactants in Nano-Emulsions." Applied Surfactants: Principles and Applications. Wiley-VCH Verlag GmbH & Co. Weinheim. ISBN: 3-527-30629-3. 2005. pp. 285-308.

Tarumoto, et al., Studies on toxicity of hydrocortisone 17-butyrate 21-propionate -1. Accute toxicity of hydrocortisone 17-butyrate 21-propionate and its analogues in mice, rats and dogs (author's trans), J Toxicol Sci., Jul. 1981; 6 Suppl: 1-16 (Abstract only).

Tata, et al., "Relative Influence of Ethanol and Propylene Glycol Cosolvents on Deposition of Minoxidil into the Skin", Journal of Pharmaceutical Sciences, 83(10):1508-1510 (1994).

Tsai, et al., "Effect of Minoxidil Concentration on the Deposition of Drug and Vehicle into the Skin", International Journal of Pharmaceutics, 96(1-3):111-117 (1993)—Abstract, 1 page.

Wermuth, C.G. "Similarity in drugs: reflections on analogue design," Drug Discovery Today, vol. 11, Nos. 7/8, Apr. 2006, pp. 348-354.

"Coal tars and coal-tar pitches," Report on Carcinogens, Twelfth Edition, 2011, 3 pages.

Adisen et al. "Topical tetracycline in the treatment of acne vulgaris," J Drugs Dermatol., 2008, 7:953-5.

Baskaran et al., "Poloxamer-188 improves capillary blood flow and tissue viability in a cutaneous burn wound," J. Surg. Res., 2001, 101(1):56-61.

Bell-Syer et al. "A systematic review of oral treatments for fungal infections of the skin of the feet," J. Dermatolog. Treat., 2001, 12:69-74.

Boehm et al. 1994, "Synthesis of high specific activity [.sup.3 H]-9-cis-retinoic acid and its application for identifying retinoids with unusual binding properties," J. Med. Chem., 37:408-414.

Carapeti et al., "Topical diltiazem and bethanechol decrease anal sphincter pressure and heal anal fissures without side effects," *Dis Colon Rectum*, 2000, 43(10):1359-62.

Cook and Mortensen, "Nifedipine for treatment of anal fissures," *Dis Colon Rectum*, 2000, 43(3):430-1.

Dumortier et al., "A review of poloxamer 407 pharmaceutical and pharmacological characteristics," *Pharmaceutical Res.*, 2006, 23(12):2709-2728.

Ebadi et al., "Healing effect of topical nifedipine on skin wounds of diabetic rats," *DARU*, 2003, 11(1):19-22.

Effendy and Maibach. "Surfactants and Experimental Irritant Contact Dermatitis." *Contact Dermatol.*, 1995, 33:217-225

Elias and Ghadially, "The aged epidermal permeability barrier," *Clinical Geriatric Medicine*, Feb. 2002, pp. 103-120

Fantin et al., "Critical influence of resistance to streptogramin B-type antibiotics on activity of RP 59500 (Quinupristin-dalfopristin) in experimental endocarditis due to *Staphylococcus aureus*," *Antimicrob Agents and Chemothery.* 1999, 39:400-405.

Fluhr et al., "Glycerol accelerates recovery of barrier function in vivo," *Acta Derm. Venereol*, 1999, 79:418-21.

Garti et al. "Sucrose Esters microemulsions," *J. Molec. Liquids*, 1999, 80:253-296.

Hammer et al. "Anti-Microbial Activity of Essential Oils and other Plant extracts," *J. Applied Microbiology*, 1999, 86:985-990.

Hwang et al. "Isolation and identification of mosquito repellents in *Artemisia vulgaris*," *J. Chem Ecol.*, 11: 1297-1306, 1985.

Knight et al., "Topical diltiazem ointment in the treatment of chronic anal fissure," *Br. J. Surg.*, 2001, 88(4):553-6.

Kucharekova et al., "Effect of a lipid-rich emollient containing ceramide 3 in experimentally induced skin barrier dysfunction," *Contact Dermatitis*, Jun. 2002, pp. 331-338.

Leive et al, "Tetracyclines of various hydrophobicities as a probe for permeability of *Escherichia coli* outer membrane," *Antimicrobial Agents and Chemotherapy*, 1984, 25:539-544.

Luepke and Kemper, "The HET-CAM Test: An Alternative to the Draize Eye Test," *FD Chem Toxic.*, 1986, 24:495-196.

Osborne and Henke, "Skin Penetration Enhancers Cited in the Technical Literature," *Pharm Technology*, Nov. 1997, pp. 58-86.

Padi. "Minocycline prevents the development of neuropathic pain, but not acute pain: possible anti-inflammatory and antioxidant mechanisms," *Eur J. Pharmacol*, 2008, 601:79-87.

Palamaras and Kyriakis, "Calcium antagonists in dermatology: a review of the evidence and research-based studies," *Derm. Online Journal*, 2005, 11(2):8.

Passi et al., Lipophilic antioxidants in 471-477 human sebum and aging, *Free Radical Research*, 2002, pp. 471-477.

Perrotti et al., "Topical Nifedipine With Lidocaine Ointment vs. Active Control for Treatment of Chronic Anal Fissure," *Dis Colon Rectum*, 2002, 45(11):1468-1475.

Repa et al. "All-trans-retinol is a ligand for the retinoic acid receptors," *Proc. Natl. Acad Sci, USA*, 90: 7293-7297, 1993.

Ruledge, "Some corrections to the record on insect repellents and attractants," *J. Am. Mosquito Control Assoc*, 1988, 4(4): 414-425.

Sakai et al., "Characterization of the physical properties of the stratum corneum by a new tactile sensor," *Skin Research and Technology*, Aug. 2000, pp. 128-134.

Schaefer, "Silicone Surfactants," *Tenside, Surfactants, Deterg.*, 1990, 27(3): 154-158.

Simoni et al., "Retinoic acid and analogs as potent inducers of differentiation and apoptosis. New promising chemopreventive and chemotherapeutic agents in oncology," *Pure Appl Chem.*, 2001, 73(9):1437-1444.

Smith, "Hydroxy acids and skin again," *Soap Cosmetics Chemical Specialties*, 1993, pp. 54-59.

Solans et al. "Overview of basic aspects of microemulsions," Industrial Applications of Microemulsions, Solans et al Eds, New York, 1997, 66:1-17.

Squillante et al., "Codiffusion of propylene glycol and dimethyl isosorbide in hairless mouse skin," *European J. Pharm. Biopharm.*, 1998, 46(3):265-71.

Todd et al. "Volatile Silicone Fluids for Cosmetics," *91 Cosmetics and Toiletries*, 1976, 27-32.

Torma et al., "Biologic activities of retinoic acid and 3, 4-dehydroretinoic acid in human keratinoacytes are similar and correlate with receptor affinities and transactivation properties," *J. Invest. Dermatology*, 1994, 102: 49-54.

USP23/NF 18The United States Pharmacopeia: The National Formulary, US Pharmacopoeia, 1995, p. 10-14.

Van Slyke, "On the measurement of buffer values and on the relationship of buffer value to the dissociation constant of the buffer and the concentration and reaction of the buffer solution," *J. Biol. Chem.*, 1922, 52:525-570.

Van Cutsem et al., "The antiinflammatory efects of ketoconazole," *J. AM. ACAD. Dermatol.*, 1991, 25(2 pt 1):257-261.

Wang and Chen, "Preparation and surface active properties of biodegradable dextrin derivative surfactants," *Colloids and Surfaces A: Physicochemical and Engineering Aspects*, 2006, 281(1- 3): 190-193.

Weindl et al., "Hyaluronic acid in the treatment and prevention of skin diseases: molecular biological, pharmaceutical and clinical aspects," *Skin Pharmacology and Physiology*, 2004, 17: 207-213.

Xynos et al., "Effect of nifedipine on rectoanal motility," *Dis Colon Rectum*, 1996, 39(2):212-216.

Yamada et al., "Candesartan, an angiotensin II receptor antagonist, suppresses pancreatic inflammation and fibrosis in rats," *J. Pharmacol. Exp. Ther.*, 2003, 307(1)17-23.

Paragraph E.3.1 of regulation (EC) No 2003 (See Directive 67/548/EEC OJ 196, 16.8, 1967, p. 1.

Tzen et al., Lipids, proteins and structure of seed oil bodies from diverse species; *Plant Physiol.*, 1993, 101:267-276.

Brown et al. "Structural dependence of flavonoid interactions with Cu2+ inos: implications for their antioxidant properties," *Biochem. J.*, 1998, 330:1173-1178.

Cloez-Tayarani. et al., "Differential effect of serotonin on cytokine production in lipopolysaccharide-stimulated human peripheral blood mononuclear cells: involvement of 5-hydroxytryptamine2A receptors," *Int. Immunol.*, 2003, 15:233-40.

"Mineral oil USP," Chemical Abstracts Service Registry No. 8012-95-1, 2011, 7 pages.

"Tea tree oil," Chemical Abstract No. 68647-73-4, 2012, 2 pages.

Lin et al., "Ferulic acid stabilizes a solution of vitamins c and e and doubles its protoprotection of skin," *J Invest Dermatol*, 2005, 125:826-32.

Material Safety Data Sheet, Science Lab.com, Polyethylene Glycol 1000, MSDS, Nov. 6, 2008, 6 pages.

\* cited by examiner

MOISTURIZING FOAM CONTAINING LANOLIN

CROSS REFERENCE TO RELATED APPLICATIONS

This application is a continuation-in-part application of co-pending International Patent Application No. IB03/005527, designating the United States and filed on Oct. 24, 2003, which claims the benefit of priority under 35 U.S.C. §119(e) to U.S. Patent Application Ser. No. 60/429,546, filed on Nov. 29, 2002, both entitled "Cosmetic and Pharmaceutical Foam," and which claims the benefit of priority under 35 USC §119(a) to Israeli Patent Appl. No. 152486, filed Oct. 25, 2002, all of which are hereby incorporated in their entirety by reference.

This application is a continuation-in-part application of co-pending U.S. patent application Ser. No. 10/911,367, filed on Aug. 4, 2004, which claims the benefit of priority under 35 U.S.C. §119(e) to U.S. Patent Application Ser. No. 60/492,385, filed on Aug. 4, 2003, both entitled "Foam Carrier Containing Amphiphilic Copolymer Gelling Agent" and both hereby incorporated in their entirety by reference.

BACKGROUND OF THE INVENTION

Foams and, in particular, foam emulsions are complex dispersion systems which do not form under all circumstances. Slight shifts in foam emulsion composition, such as by the addition of active ingredients, may destabilize the foam.

There have been a few attempts to create foams containing lanolin.

U.S. Pat. No. 5,679,324 pertains to an aerosol foamable fragrance composition, translucent in its pre-dispensed state, which forms a fast-breaking foam. The composition contains a surfactant selected from the group consisting of ethoxylated lanolin oil derivatives, propoxylated lanolin oil derivatives, and mixtures thereof, a propellant, a fragrance, a thickener, and a cosmetic vehicle (preferably water). Emollients may be included, however, being translucent, the composition cannot comprise significant oil concentrations (which would make it opaque). Apparently the foam breaks spontaneously upon discharging from an aerosol container (with no need of any rubbing or sheer force application), thus making it impractical for certain applications such as intravaginal applications.

SUMMARY OF THE INVENTION

The present invention provides a highly tolerable, hydrating lanolin containing foamable composition product for administration to the skin, a body surface, a body cavity or mucosal surface, e.g., the mucosa of the nose, mouth, eye, ear, respiratory system, vagina or rectum (the "target site"). The foamable composition includes lanolin, a surface-active agent, about 0.01% to about 5% by weight of at least one polymeric additive selected from the group consisting of a bioadhesive agent, a gelling agent, a film forming agent and a phase change agent, water, and a liquefied or compressed gas propellant at a concentration of about 3% to about 25% by weight of the total composition. The hydrating lanolin foam composition absorbs and stores water from the environment to thereby hydrate the target site.

According to further embodiments of the present invention, the foamable composition further contains at least one organic carrier selected from the group consisting of a hydrophobic organic carrier, a polar solvent, an emollient and mixtures thereof, wherein the at least one organic carrier is present in an amount selected from the group consisting of about 2% to about 5%, about 5% to about 10%, about 10% to about 20%, and about 20% to about 50%.

According to further embodiments of the present invention, lanolin is selected from the group consisting of lanolin, wool fat, lanolin wax and hydrophobic derivatives thereof.

According to further embodiments of the present invention, there is provided a method of treating, alleviating or preventing a disorders of the skin, a body cavity or mucosal surface, wherein the disorder involves insufficient hydration as one of its etiological factors. The method includes administering topically to a subject having the disorder, a foamed composition including lanolin, about 0.1% to about 5% by weight of a surface-active agent, about 0.01% to about 5% by weight of a polymeric additive selected from a bioadhesive agent, a gelling agent, a film forming agent and a phase change agent, and water.

According to still further embodiments of method according to the present invention, the composition further includes at least one additional therapeutic agent.

According to yet further embodiments of method according to the present invention, the organic carrier includes at least one therapeutically active oil.

BRIEF DESCRIPTION OF THE DRAWING

The invention is described with reference to the figures, which are presented for the purpose of illustration and are not intended to be limiting of the invention.

DETAILED DESCRIPTION OF THE INVENTION

Figure 1:
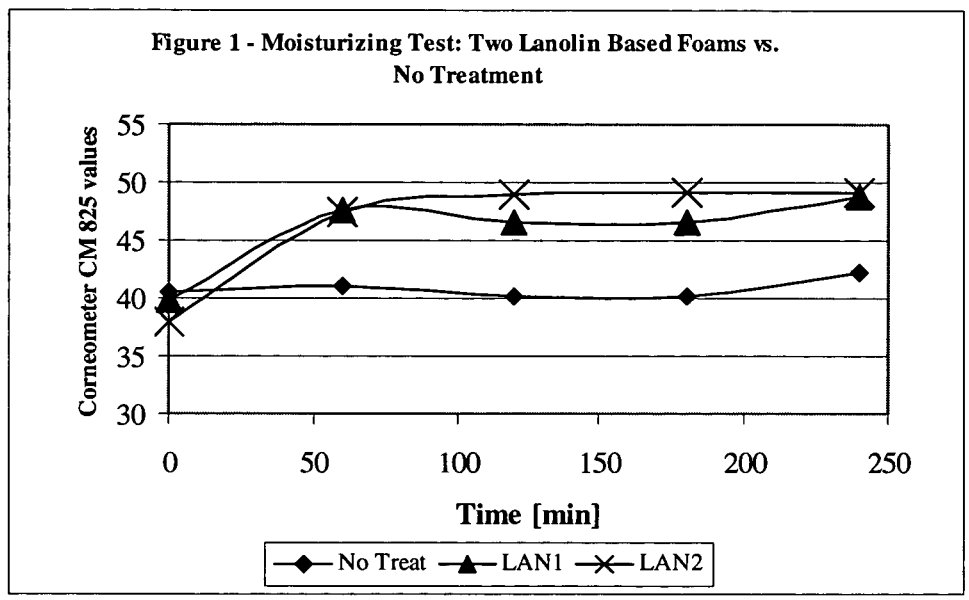
FIG. 1 is a plot of hydration value vs. time for two foamed lanolin compositions, illustrating the skin hydrating effect of two lanolin-containing foams.

The present invention provides a highly tolerable, hydrating lanolin-containing foamable composition product.

All % values are provided on a weight (w/w) basis.

According to one or more embodiments of the present invention, the foamable lanolin containing composition for administration to the skin, a body surface, a body cavity or mucosal surface, e.g., the mucosa of the nose, mouth, eye, ear, respiratory system, vagina or rectum (severally and interchangeably termed herein "target site") includes:

(1) lanolin;
(2) about 0.1% to about 5% by weight of a surface-active agent;
(3) about 0.01% to about 5% by weight of at least one polymeric agent selected from a bioadhesive agent, a gelling agent, a film forming agent and a phase change agent; and
(4) a liquefied or compressed gas propellant at a concentration of about 3% to about 25% by weight of the total composition.

Water and optional ingredients are added to complete the total mass to 100%. Upon release from an aerosol container, the foamable composition forms an expanded foam suitable for topical administration.

Lanolin, also termed "wool fat" and "wool fat alcohols" is a hydrophobic greasy, substance extracted from wool, produced from the oil glands of sheep. Lanolin wax is a high melting wax fraction separated from lanolin, and white lanolin is obtained by further purifications to obtain desired lanolin fractions or derivatives.

Natural lanolin is produced, among other methods, by extraction from the wool by kneading with water, with which it readily forms an emulsion. On heating, it separates as a distinct layer at the surface of the liquid. Purification is effected by repeated treatment with water in a centrifugal machine, or by some other suitable process.

The constituents of lanolin include cholesterol and isocholesterol, together with various esters of cholesterol and/or isocholesterol with one or more fatty acids, including, but not limited to lanoceric acid, lanopalmitic acid, carnaubic acid, myristic acid, oleic acid, cerotic acid and palmitic acid.

In one or more embodiments of the present invention, lanolin is a synthetic lanolin or a synthetic lanolin derivative. In the context of the present invention, a synthetic lanolin or a synthetic lanolin derivative is a hydrophobic derivative of lanolin, which is the result of a chemical or biochemical modification of natural lanolin. Synthetic lanolin or a synthetic lanolin derivative may consist of cholesterol or isocholesterol covalently linked with an organic moiety. By way of non-limiting examples, synthetic lanolin derivatives include organic alcohols derived from the hydrolysis of lanolin, esters of lanolin with an aliphatic acid (e.g., acetylated lanolin), lanolin acid (a mixture of organic acids obtained from the hydrolysis of lanolin), esters of lanolin with aliphatic alcohols (e.g., isopropyl lanolate and cetyl lanolate).

The presence of lanolin may be determined by detection of cholesterol, a compound making up lanolin. To test, one gram of a fat is dissolved in 3 or 4 mL of acetic anhydride and 0.3 mL of sulfuric acid, resulting in a pink coloration, further changing to green and blue.

Optionally, the composition further contains at least one organic carrier selected from a hydrophobic organic carrier, a polar solvent, an emollient and mixtures thereof, at a concentration of about 2% to about 5%, or about 5% to about 10%, or about 10% to about 20%, or about 20% to about 50% by weight.

A "hydrophobic organic carrier" as used herein refers to a material having solubility in distilled water at ambient temperature of less than about 1 gm per 100 mL, more preferable less than about 0.5 gm per 100 mL, and most preferably less than about 0.1 gm per 100 mL. It is liquid at ambient temperature. The identification of a hydrophobic organic carrier or "hydrophobic solvent", as used herein, is not intended to characterize the solubilization capabilities of the solvent for any specific active agent or any other component of the foamable composition. Rather, such information is provided to aid in the identification of materials suitable for use as a hydrophobic carrier in the foamable compositions described herein.

In one or more embodiments, the hydrophobic organic carrier is an oil, such as mineral oil. Mineral oil (Chemical Abstracts Service Registry number 8012-95-1) is a mixture of aliphatic, naphthalenic, and aromatic liquid hydrocarbons that derive from petroleum. It is typically liquid; its viscosity is in the range of between about 35 CST and about 100 CST (at 40° C.), and its pour point (the lowest temperature at which an oil can be handled without excessive amounts of wax crystals forming so preventing flow) is below 0° C. In one or more embodiments, the term hydrophobic organic carrier does not include thick or semi-solid materials, such as white petrolatum, also termed "Vaseline", which, in certain compositions is disadvantageous due to its waxy nature and semi-solid texture.

According to one or more embodiments, hydrophobic solvents are liquid oils originating from vegetable, marine or animal sources. Suitable liquid oil includes saturated, unsaturated or polyunsaturated oils. By way of example, the unsaturated oil may be olive oil, corn oil, soybean oil, canola oil, cottonseed oil, coconut oil, sesame oil, sunflower oil, borage seed oil, syzigium aromaticum oil, hempseed oil, herring oil, cod-liver oil, salmon oil, flaxseed oil, wheat germ oil, evening primrose oils or mixtures thereof, in any proportion.

Suitable hydrophobic solvents also include polyunsaturated oils containing poly-unsaturated fatty acids. In one or more embodiments, said unsaturated fatty acids are selected from the group of omega-3 and omega-6 fatty acids. Examples of such polyunsaturated fatty acids are linoleic and linolenic acid, gamma-linoleic acid (GLA), eicosapentaenoic acid (EPA) and docosahexaenoic acid (DHA). Such unsaturated fatty acids are known for their skin-conditioning effect, which contribute to the therapeutic benefit of the present foamable composition. Thus, the hydrophobic solvent can include at least 6% of an oil selected from omega-3 oil, omega-6 oil, and mixtures thereof. In the context of the present invention, oils that possess therapeutically beneficial properties are termed "therapeutically active oil".

Another class of hydrophobic solvents is the essential oils, which are also considered therapeutically active oil, which contain active biologically occurring molecules and, upon topical application, exert a therapeutic effect, which is conceivably synergistic to the beneficial effect of the NSAID in the composition.

Another class of therapeutically active oils includes liquid hydrophobic plant-derived oils, which are known to possess therapeutic benefits when applied topically.

Silicone oils also may be used and are desirable due to their known skin protective and occlusive properties. Suitable silicone oils include non-volatile silicones, such as polyalkyl siloxanes, polyaryl siloxanes, polyalkylaryl siloxanes and polyether siloxane copolymers, polydimethylsiloxanes (dimethicones) and poly(dimethylsiloxane)-(diphenyl-siloxane) copolymers. These are chosen from cyclic or linear polydimethylsiloxanes containing from about 3 to about 9, preferably from about 4 to about 5, silicon atoms. Volatile silicones such as cyclomethicones can also be used. Silicone oils are also considered therapeutically active oil, due to their barrier retaining and protective properties.

In one or more embodiments, the hydrophobic carrier includes at least 2% by weight silicone oil or at least 5% by weight.

The solvent may be a mixture of two or more of the above hydrophobic solvents in any proportion.

A further class of solvents includes "emollients" that have a softening or soothing effect, especially when applied to body areas, such as the skin and mucosal surfaces. Emollients are not necessarily hydrophobic. Examples of suitable emollients include hexyleneglycol, propylene glycol, isostearic acid derivatives, isopropyl palmitate, isopropyl isostearate, diisopropyl adipate, diisopropyl dimerate, maleated soybean oil, octyl palmitate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, isononyl isononanoate, isotridecyl isononanoate, myristyl myristate, triisocetyl citrate, octyl dodecanol, sucrose esters of fatty acids, octyl hydroxystearate and mixtures thereof.

According to one or more embodiments of the present invention, the hydrophobic organic carrier includes a mixture of a hydrophobic solvent and an emollient. According to one or more embodiments, the foamable composition is a mixture of mineral oil and an emollient in a ratio between 2:8 and 8:2 on a weight basis.

A "polar solvent" is an organic solvent, typically soluble in both water and oil. Examples of polar solvents include polyols, such as glycerol (glycerin), propylene glycol, hexylene glycol, diethylene glycol, propylene glycol n-alkanols, terpenes, di-terpenes, tri-terpenes, terpen-ols, limonene, terpene-ol, 1-menthol, dioxolane, ethylene glycol, other glycols, sulfoxides, such as dimethylsulfoxide (DMSO), dimethylformanide, methyl dodecyl sulfoxide, dimethylacetamide, monooleate of ethoxylated glycerides (with 8 to 10 ethylene oxide units), azone (1-dodecylazacycloheptan-2-one), 2-(n-nonyl)-1,3-dioxolane, esters, such as isopropyl myristate/palmitate, ethyl acetate, butyl acetate, methyl proprionate, capric/caprylic triglycerides, octylmyristate, dodecyl-myristate; myristyl alcohol, lauryl alcohol, lauric acid, lauryl lactate ketones; amides, such as acetamide oleates such as triolein; various alkanoic acids such as caprylic acid; lactam compounds, such as azone; alkanols, such as dialkylamino acetates, and admixtures thereof.

According to one or more embodiments, the polar solvent is a polyethylene glycol (PEG) or PEG derivative that is liquid at ambient temperature, including PEG200 (MW (molecular weight) about 190-210 kD), PEG300 (MW about 285-315 kD), PEG400 (MW about 380-420 kD), PEG600 (MW about 570-630 kD) and higher MW PEGs such as PEG 4000, PEG 6000 and PEG 10000 and mixtures thereof.

According to one or more embodiments, the foamable composition is substantially alcohol-free, i.e., free of short chain alcohols. Short chain alcohols, having up to 5 carbon atoms in their carbon chain skeleton and one hydroxyl group, such as ethanol, propanol, isopropanol, butanol, iso-butanol, t-butanol and pentanol, are considered less desirable solvents or polar solvents due to their skin-irritating effect. Thus, the composition is substantially alcohol-free and includes less than about 5% final concentration of lower alcohols, preferably less than about 2%, more preferably less than about 1%.

The polymeric agent serves to stabilize the foam composition and to control drug residence in the target organ. Exemplary polymeric agents, are classified below in a non-limiting manner. In certain cases, a given polymer can belong to more than one of the classes provided below.

In one or more embodiments, the composition of the present invention includes at least one gelling agent. A gelling agent controls the residence of a therapeutic composition in the target site of treatment by increasing the viscosity of the composition, thereby limiting the rate of its clearance from the site. Many gelling agents are known in the art to possess mucoadhesive properties.

The gelling agent can be a natural gelling agent, a synthetic gelling agent and an inorganic gelling agent. Exemplary gelling agents that can be used in accordance with one or more embodiments of the present invention include, for example, naturally-occurring polymeric materials, such as locust bean gum, sodium alginate, sodium caseinate, egg albumin, gelatin agar, carrageenin gum, sodium alginate, xanthan gum, quince seed extract, tragacanth gum, guar gum, starch, chemically modified starches and the like, semi-synthetic polymeric materials such as cellulose ethers (e.g. hydroxyethyl cellulose, methyl cellulose, carboxymethyl cellulose, hydroxy propylmethyl cellulose), guar gum, hydroxypropyl guar gum, soluble starch, cationic celluloses, cationic guars, and the like, and synthetic polymeric materials, such as carboxyvinyl polymers, polyvinylpyrrolidone, polyvinyl alcohol, polyacrylic acid polymers, polymethacrylic acid polymers, polyvinyl acetate polymers, polyvinyl chloride polymers, polyvinylidene chloride polymers and the like. Mixtures of the above compounds are contemplated.

Further exemplary gelling agents include the acrylic acid/ethyl acrylate copolymers and the carboxyvinyl polymers sold, for example, by the B.F. Goodrich Company under the trademark of Carbopol® resins. These resins consist essentially of a colloidal water-soluble polyalkenyl polyether crosslinked polymer of acrylic acid crosslinked with from 0.75% to 2% of a crosslinking agent such as polyallyl sucrose or polyallyl pentaerythritol. Examples include Carbopol® 934, Carbopol® 940, Carbopol® 950, Carbopol® 980, Carbopol® 951 and Carbopol® 981. Carbopol® 934 is a water-soluble polymer of acrylic acid crosslinked with about 1% of a polyallyl ether of sucrose having an average of about 5.8 allyl groups for each sucrose molecule.

In one or more embodiment, the composition of the present invention includes at least one polymeric agent, which is a water-soluble cellulose ether. Preferably, the water-soluble cellulose ether is selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose and carboxymethylhydroxyethylcellulose. More preferably, the water-soluble cellulose ether is selected from the group consisting of methylcellulose, hydroxypropyl cellulose and hydroxypropyl methylcellulose (Methocel). In one or more embodiments, the composition includes a combination of a water-soluble cellulose ether; and a naturally-occurring polymeric materials, selected from the group including xanthan gum, guar gum, carrageenan gum, locust bean gum and tragacanth gum.

Yet, in other embodiments, the gelling agent includes inorganic gelling agents, such as silicone dioxide (fumed silica).

Mucoadhesion/bioadhesion is defined as the attachment of synthetic or biological macromolecules to a biological tissue. Mucoadhesive agents are a class of polymeric biomaterials that exhibit the basic characteristic of a hydrogel, i.e. swell by absorbing water and interacting by means of adhesion with the mucous that covers epithelia. Compositions of the present invention may contain a mucoadhesive macromolecule or polymer in an amount sufficient to confer bioadhesive properties. The bioadhesive macromolecule enhances the delivery of biologically active agents on or through the target surface. The mucoadhesive macromolecule may be selected from acidic synthetic polymers, preferably having at least one acidic group per four repeating or monomeric subunit moieties, such as poly(acrylic)- and/or poly(methacrylic) acid (e.g., Carbopol®, Carbomer®), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl)methylcellulose; basic amine-bearing polymers such as chitosan; acidic polymers obtainable from natural sources, such as alginic acid, hyaluronic acid, pectin, gum tragacanth, and karaya gum; and neutral synthetic polymers, such as polyvinyl alcohol or their mixtures. An additional group of mucoadhesive polymers includes natural and chemically modified cyclodextrin, especially hydroxypropyl-β-cyclodextrin. Such polymers may be present as free acids, bases, or salts, usually in a final concentration of about 0.01% to about 0.5% by weight.

A suitable bioadhesive macromolecule is the family of acrylic acid polymers and copolymers, (e.g., Carbopol®).

These polymers contain the general structure —[CH$_2$—CH(COOH)—]$_n$. Hyaluronic acid and other biologically-derived polymers may be used.

Exemplary bioadhesive or mucoadhesive macromolecules have a molecular weight of at least 50 kDa, or at least 300 kDa, or at least 1,000 kDa. Favored polymeric ionizable macromolecules have not less than 2 mole percent acidic groups (e.g., COOH, SO3H) or basic groups (NH2, NRH, NR2), relative to the number of monomeric units. The acidic or basic groups can constitute at least 5 mole percent, or at least 10 mole percent, or at least 25, at least 50 more percent, or even up to 100 mole percent relative to the number of monomeric units of the macromolecule.

Yet, another group of mucoadhesive agent includes inorganic gelling agents such as silicon dioxide (fumed silica), including but not limited to, AEROSIL 200 (DEGUSSA).

Many mucoadhesive agents are known in the art to also possess gelling properties.

The foam composition may contain a film forming component. The film forming component may include at least one water-insoluble alkyl cellulose or hydroxyalkyl cellulose. Exemplary alkyl cellulose or hydroxyalkyl cellulose polymers include ethyl cellulose, propyl cellulose, butyl cellulose, cellulose acetate, hydroxypropyl cellulose, hydroxybutyl cellulose, and ethylhydroxyethyl cellulose, alone or in combination. In addition, a plasticizer or a cross linking agent may be used to modify the polymer's characteristics. For example, esters such as dibutyl or diethyl phthalate, amides such as diethyldiphenyl urea, vegetable oils, fatty acids and alcohols such as oleic and myristyl acid may be used in combination with the cellulose derivative.

In one or more embodiments, the composition of the present invention includes a phase change polymer, which alters the composition behavior from fluid-like prior to administration to solid-like upon contact with the target mucosal surface. Such phase change results from external stimuli, such as changes in temperature or pH and exposure to specific ions (e.g., Ca$^{2+}$).

Non-limiting examples of phase change polymers include poly(N-isopropylamide), Poloxamer 407® and Smart-Gel® (Poloxamer+PAA)

The polymeric agent is present in an amount in the range of about 0.01% to about 5.0% by weight of the foam composition. In one or more embodiments, it is typically less than about 1 wt % of the foamable composition.

Surface-active agents (also termed "surfactants") include any agent linking oil and water in the composition, in the form of emulsion. A surfactant's hydrophilic/lipophilic balance (HLB) describes the emulsifier's affinity toward water or oil. The HLB scale ranges from 1 (totally lipophilic) to 20 (totally hydrophilic), with 10 representing an equal balance of both characteristics. Lipophilic emulsifiers form water-in-oil (w/o) emulsions; hydrophilic surfactants form oil-in-water (o/w) emulsions. The HLB of a blend of two emulsifiers equals the weight fraction of emulsifier A times its HLB value plus the weight fraction of emulsifier B times its HLB value (weighted average).

According to one or more embodiments of the present invention, the surface-active agent has a hydrophilic lipophilic balance (HLB) between about 9 and about 14, which is the required HLB (the HLB required to stabilize an O/W emulsion of a given oil) of most oils and hydrophobic solvents. Thus, in one or more embodiments, the composition contains a single surface active agent having an HLB value between about 9 and 14, and in one or more embodiments, the composition contains more than one surface active agent and the weighted average of their HLB values is between about 9 and about 14. Yet, in other embodiments, when a water in oil emulsion is desirable, the composition contains one or more surface active agents, having an HLB value between about 2 and about 9.

The surface-active agent is selected from anionic, cationic, nonionic, zwitterionic, amphoteric and ampholytic surfactants, as well as mixtures of these surfactants. Such surfactants are well known to those skilled in the therapeutic and cosmetic formulation art. Nonlimiting examples of possible surfactants include polysorbates, such as polyoxyethylene (20) sorbitan monostearate (Tween 60) and poly(oxyethylene) (20) sorbitan monooleate (Tween 80); poly(oxyethylene) (POE) fatty acid esters, such as Myrj 45, Myrj 49, Myrj 52 and Myrj 59; poly(oxyethylene)alkylyl ethers, such as poly(oxyethylene)cetyl ether, poly(oxyethylene)palmityl ether, polyethylene oxide hexadecyl ether, polyethylene glycol cetyl ether, brij 38, brij 52, brij 56 and brij W1; sucrose esters, partial esters of sorbitol and its anhydrides, such as sorbitan monolaurate and sorbitan monolaurate; mono or diglycerides, isoceteth-20, sodium methyl cocoyl taurate, sodium methyl oleoyl taurate, sodium lauryl sulfate, triethanolamine lauryl sulfate and betaines.

In one or more embodiments of the present invention, the surface-active agent includes at least one non-ionic surfactant. Ionic surfactants are known to be irritants. Therefore, non-ionic surfactants are preferred in applications including sensitive tissue such as found in most mucosal tissues, especially when they are infected or inflamed. We have surprisingly found that non-ionic surfactants alone provide foams of excellent quality, i.e. a score of "E" according to the grading scale discussed herein below.

In one or more embodiments, the surface active agent includes a mixture of at least one non-ionic surfactant and at least one ionic surfactant in a ratio in the range of about 100:1 to 6:1. In one or more embodiments, the non-ionic to ionic surfactant ratio is greater than about 6:1, or greater than about 8:1; or greater than about 14:1, or greater than about 16:1, or greater than about 20:1.

In one or more embodiments of the present invention, a combination of a non-ionic surfactant and an ionic surfactant (such as sodium lauryl sulphate and cocamidopropylbetaine) is employed, at a ratio of between 1:1 and 20:1, or at a ratio of 4:1 to 10:1. The resultant foam has a low specific gravity, e.g., less than 0.1 g/ml.

It has been surprisingly discovered that the stability of the composition is especially pronounced when a combination of at least one non-ionic surfactant having HLB of less than 9 and at least one non-ionic surfactant having HLB of equal or more than 9 is employed. The ratio between the at least one non-ionic surfactant having HLB of less than 9 and the at least one non-ionic surfactant having HLB of equal or more than 9, is between 1:8 and 8:1, or at a ratio of 4:1 to 1:4. The resultant HLB of such a blend of at least two emulsifiers is between about 9 and about 14.

Thus, in an exemplary embodiment, a combination of at least one non-ionic surfactant having HLB of less than 9 and at least one non-ionic surfactant having HLB of equal or more than 9 is employed, at a ratio of between 1:8 and 8:1, or at a ratio of 4:1 to 1:4, wherein the HLB of the combination of emulsifiers is between about 9 and about 14.

In one or more embodiments of the present invention, the surface-active agent includes mono-, di- and tri-esters of sucrose with fatty acids (sucrose esters), prepared from sucrose and esters of fatty acids or by extraction from sucroglycerides. Suitable sucrose esters include those having high monoester content, which have higher HLB values.

The total surface active agent is in the range of about 0.1 to about 5% of the foamable composition, and is typically less than about 2% or less than about 1%.

Preferably, a therapeutically effective foam adjuvant is included in the foamable compositions of the present invention to increase the foaming capacity of surfactants and/or to stabilize the foam. In one or more embodiments of the present invention, the foam adjuvant agent includes fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), 1-triacontanol (C30), as well as alcohols with longer carbon chains (up to C50). Fatty alcohols, derived from beeswax and including a mixture of alcohols, a majority of which has at least 20 carbon atoms in their carbon chain, are especially well suited as foam adjuvant agents. The amount of the fatty alcohol required to support the foam system is inversely related to the length of its carbon chains. Foam adjuvants, as defined herein are also useful in facilitating improved spreadability and absorption of the composition.

In one or more embodiments of the present invention, the foam adjuvant agent includes fatty acids having 16 or more carbons in their carbon chain, such as hexadecanoic acid (C16) stearic acid (C18), arachidic acid (C20), behenic acid (C22), octacosanoic acid (C28), as well as fatty acids with longer carbon chains (up to C50), or mixtures thereof. As for fatty alcohols, the amount of fatty acids required to support the foam system is inversely related to the length of its carbon chain.

Optionally, the carbon atom chain of the fatty alcohol or the fatty acid may have at least one double bond. A further class of foam adjuvant agent includes a branched fatty alcohol or fatty acid. The carbon chain of the fatty acid or fatty alcohol also can be substituted with a hydroxyl group, such as 12-hydroxy stearic acid.

An important property of the fatty alcohols and fatty acids used in context of the composition of the present invention is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, anti-infective, antiproliferative and antiinflammatory properties (see, for example, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties. Long chain fatty acids have also been reported to possess anti-infective characteristics.

Thus, in preferred embodiments of the present invention, a combined and enhanced therapeutic effect is attained by including both a nonsteroidal immunomodulating agent and a therapeutically effective foam adjuvant in the same composition, thus providing a simultaneous anti-inflammatory and antiinfective effect from both components. Furthermore, in a further preferred embodiment, the composition concurrently comprises a nonsteroidal immunomodulating agent, a therapeutically effective foam adjuvant and a therapeutically active oil, as detailed above. Such combination provides an even more enhanced therapeutic benefit. Thus, the foamable carrier, containing the foam adjuvant provides an extra therapeutic benefit in comparison with currently used vehicles, which are inert and non-active.

The foam adjuvant according to preferred embodiments of the present invention includes a mixture of fatty alcohols, fatty acids and hydroxy fatty acids and derivatives thereof in any proportion, providing that the total amount is 0.1% to 5% (w/w) of the carrier mass. More preferably, the total amount is 0.4%-2.5% (w/w) of the carrier mass.

The therapeutic foam of the present invention may further optionally include a variety of formulation excipients, which are added in order to fine-tune the consistency of the formulation, protect the formulation components from degradation and oxidation and modify their consistency. Such excipients may be selected, for example, from stabilizing agents, antioxidants, humectants, preservatives, colorant and odorant agents and other formulation components, used in the art of formulation.

Aerosol propellants are used to generate and administer the foamable composition as a foam. The total composition including propellant, foamable compositions and optional ingredients is referred to as the foamable carrier. The propellant makes up about 3% to about 25 wt % of the foamable carrier. Examples of suitable propellants include volatile hydrocarbons such as butane, propane, isobutane or mixtures thereof, and fluorocarbon gases.

Several disorders of the skin, body cavity or mucosal surface (e.g., the mucosa of the nose, mouth, eye, ear, vagina or rectum), involve a combination of dry and scaly skin, which can be treated with lanolin as the hydrating component of the composition and additional therapeutic modalities that address other etiological factors of the disorder. For example, psoriasis involves dry and scaly skin, as well as inflammation, excessive cell proliferation and inadequate cell differentiation, which can be alleviated by treatment with lanolin and an additional active agent, such as a steroid, a retinoid or an alpha or beta hydroxy acid. Likewise, atopic dermatitis involves skin dryness and inflammation, which may be treated with lanolin and a steroid or an immunomodulating agent.

Thus, in one or more embodiments, the composition of the present invention is a carrier of a cosmetically or pharmaceutically active agents. Exemplary, non binding and cosmetically or pharmaceutically active agents include, but are not limited to an anti-infective, an antibiotic, an antibacterial agent, an antifungal agent, an antiviral agent, an antiparasitic agent, an steroidal antiinflammatory agent, an immunosuppressive agent, an immunomodulator, an immunoregulating agent, a hormonal agent, vitamin A, a vitamin A derivative, vitamin B, a vitamin B derivative, vitamin C, a vitamin C derivative, vitamin D, a vitamin D derivative, vitamin E, a vitamin E derivative, vitamin F, a vitamin F derivative, vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, an anti-wrinkle agent, a radical scavenger, a metal oxide (e.g., titanium dioxide, zinc oxide, zirconium oxide, iron oxide), silicone oxide, an anti wrinkle agent, a skin whitening agent, a skin protective agent, a masking agent, an anti-wart agent, a refatting agent, a lubricating agent and mixtures thereof.

Composition and Foam Physical Characteristics

A pharmaceutical or cosmetic composition manufactured using the foam carrier according to one or more embodiments of the present invention is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

The foam composition of the present invention creates a stable emulsion having an acceptable shelf-life of at least one year, or at least two years at ambient temperature. A feature of a product for cosmetic or medical use is long term stability. Propellants, which are a mixture of low molecular weight hydrocarbons, tend to impair the stability of emulsions. It has been observed, however, that foam compositions according to the present invention are surprisingly stable. Following accelerated stability studies, they demonstrate desirable texture; they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing semi-solid hydrophobic solvents, e.g., white petrolatum, as the main ingredients of the oil phase of the emulsion, exhibit high viscosity and poor flowability and are inappropriate candidates for a foamable composition.

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administratable foams are typically of quality grade E or G, when released from the aerosol container. Smaller bubbles are indicative of more stable foam, which does not collapse spontaneously immediately upon discharge from the container. The finer foam structure looks and feels smoother, thus increasing its usability and appeal.

As further aspect of the foam is breakability. The breakable foam is thermally stable, yet breaks under sheer force. Sheer-force breakability of the foam is clearly advantageous over thermally-induced breakability. Thermally sensitive foams immediately collapse upon exposure to skin temperature and, therefore, cannot be applied on the hand and afterwards delivered to the afflicted area.

Another property of the foam is specific gravity, as measured upon release from the aerosol can. Typically, foams have specific gravity of less than 0.1 g/mL or less than 0.05 g/mL.

Fields of Pharmaceutical Applications

By including lanolin and optional active agents in the compositions of the present invention, the composition are useful in treating an animal or a human patient having any one of a variety of dermatological disorders that include dry and/or scaly skin as one or their etiological factors (also termed "dermatoses"), such as classified in a non-limiting exemplary manner according to the following groups:

Dermatitis including contact dermatitis, atopic dermatitis, seborrheic dermatitis, nummular dermatitis, chronic dermatitis of the hands and feet, generalized exfoliative dermatitis, stasis dermatitis; lichen simplex chronicus; diaper rash;

Bacterial infections including cellulitis, acute lymphangitis, lymphadenitis, erysipelas, cutaneous abscesses, necrotizing subcutaneous infections, staphylococcal scalded skin syndrome, folliculitis, furuncles, hidradenitis suppurativa, carbuncles, paronychial infections, erythrasma;

Fungal Infections including dermatophyte infections, yeast Infections; parasitic Infections including scabies, pediculosis, creeping eruption;

Viral Infections;

Disorders of hair follicles and sebaceous glands including acne, rosacea, perioral dermatitis, hypertrichosis (hirsutism), alopecia, including male pattern baldness, alopecia areata, alopecia universalis and alopecia totalis; pseudofolliculitis barbae, keratinous cyst;

Scaling papular diseases including psoriasis, pityriasis rosea, lichen planus, pityriasis rubra pilaris;

Benign tumors including moles, dysplastic nevi, skin tags, lipomas, angiomas, pyogenic granuloma, seborrheic keratoses, dermatofibroma, keratoacanthoma, keloid;

Malignant tumors including basal cell carcinoma, squamous cell carcinoma, malignant melanoma, paget's disease of the nipples, kaposi's sarcoma;

Reactions to sunlight including sunburn, chronic effects of sunlight, photosensitivity;

Bullous diseases including pemphigus, bullous pemphigoid, dermatitis herpetiformis, linear immunoglobulin A disease;

Pigmentation disorders including hypopigmentation such as vitiligo, albinism and postinflammatory hypopigmentation and hyperpigmentation such as melasma (chloasma), drug-induced hyperpigmentation, postinflammatory hyperpigmentation;

Disorders of cornification including ichthyosis, keratosis pilaris, calluses and corns, actinic keratosis;

Pressure sores;

Disorders of sweating; and

Inflammatory reactions including drug eruptions, toxic epidermal necrolysis; erythema multiforme, erythema nodosum, granuloma annulare.

According to one or more embodiments of the present invention, the compositions are also useful in the therapy of non-dermatological disorders by providing transdermal delivery of an active nonsteroidal immunomodulating agent that is effective against non-dermatological disorders.

The same advantage is expected when the composition is topically applied to a body cavity or mucosal surface (e.g., the mucosa of the nose, mouth, eye, ear, vagina or rectum) to treat conditions such as chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VIN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, cnal abscess/fistula, anal cancer, anal fissure, anal warts, Crohn's disease, hemorrhoids, anal itch, pruritus ani, fecal incontinence, constipation, polyps of the colon and rectum.

The following examples exemplify the therapeutic kits and pharmacological compositions and methods described herein. The examples are for the purposes of illustration only and are not intended to be limiting of the invention.

Example 1

Lanolin Based Foamable Compositions

|  | Composition No: | | | |
|---|---|---|---|---|
|  | LAN1 | LAN2 | LAN3 | LAN4 |
|  | % | | | |
| Ingredient | | | | |
| Lanolin | 5.00 | 15.00 | 30.00 | 40.00 |
| Mineral oil light | 20.00 | — | — | — |
| MCT oil | — | 10.00 | — | — |
| Glyceryl monostearate | 0.45 | 0.45 | 0.45 | 1.00 |
| Stearyl alcohol | 0.95 | — | — | — |
| Xanthan gum | 0.28 | — | — | — |
| Methocel K100M | 0.28 | — | — | — |
| Polysorbate 80 | 0.95 | 0.95 | 0.95 | 0.95 |
| PEG-40 Stearate | 2.80 | 2.80 | 2.80 | 2.80 |
| Preservative | 0.25 | 0.25 | 0.25 | 0.25 |
| Propellant | 8.00 | 8.00 | 8.00 | 8.00 |
| Water | To 100 | To 100 | To 100 | To 100 |
| Composition Properties | | | | |
| Emulsion color | White | White | White | White |
| Foam Density | 0.06 | 0.06 | 0.08 | 0.08 |

Example 2

Additional Lanolin Based Foamable Compositions

|  | Composition No: | | | |
|---|---|---|---|---|
|  | LAN5 | LAN6 | LAN7 | LAN8 |
|  | % | | | |
| Ingredient | | | | |
| Lanolin | 5.00 | 5.00 | 5.00 | 5.00 |
| Mineral oil | 20.00 | 20.00 | 20.00 | — |
| IPP | 10.00 | — | — | — |
| IPM | — | 10.00 | 10.00 | — |
| Beeswax | 2.00 | 2.00 | 2.00 | 2.00 |
| Glyceryl oleate | 0.80 | 0.80 | 0.80 | 0.80 |
| Glyceryl monostearate SE | 0.80 | 0.80 | 0.80 | 0.80 |
| Arlacel P135 | 0.40 | 0.40 | 0.40 | 0.40 |
| Ceteth-2 (Lipocol C2) | 6.00 | 5.00 | 5.00 | 5.00 |
| Arlatone 2121 | 0.50 | 0.50 | 0.50 | 0.50 |
| Sucrose ester SP30 | 0.80 | 0.80 | 0.80 | 0.80 |
| Sucrose ester SP10 | 0.80 | 0.80 | 0.80 | 0.80 |
| Aloe vera extract | 0.10 | 0.10 | 0.10 | 0.10 |
| Xanthan gum | 0.40 | 0.40 | 0.40 | 0.40 |
| Magnesium sulfate | — | 0.20 | 0.20 | 0.20 |
| D-Pantenol | 4.00 | 4.00 | 4.00 | 4.00 |
| Disodium EDTA | 0.20 | 0.40 | 0.40 | 0.40 |
| Alpha Bisabolol | — | 0.20 | 0.20 | 0.20 |
| Benzalkonium chloride (50% sol) | 0.20 | 0.20 | 0.20 | 0.20 |
| Zinc oxide | 10.00 | 10.00 | — | — |
| Water | To 100 | To 100 | To 100 | To 100 |
| Composition Properties | | | | |
| Emulsion color | White | White | White | White |
| Foam Density | 0.072 | 0.086 | 0.088 | 0.070 |

Example 6

Figure 2:
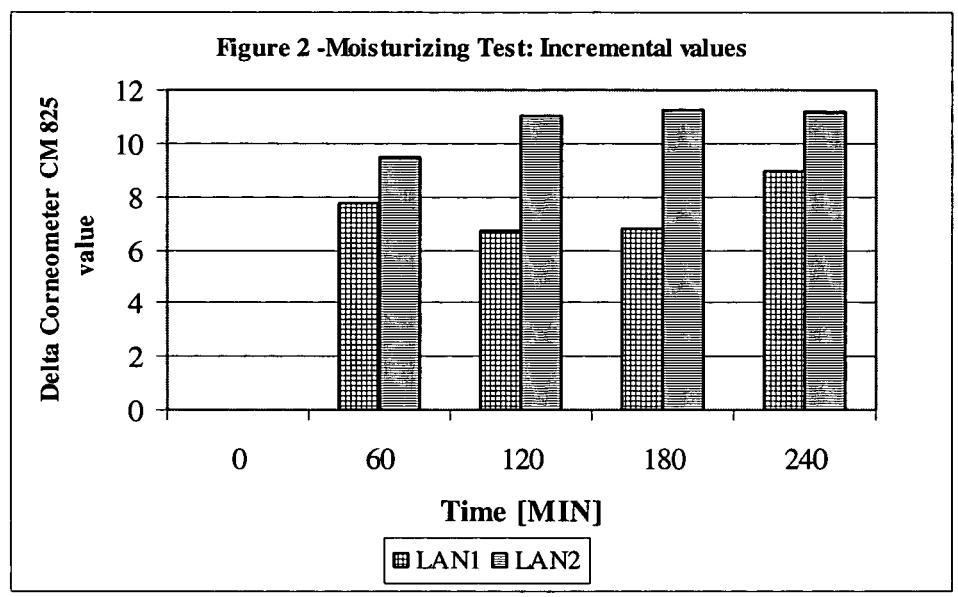
FIG. 2 is a bar graph illustrating the difference in skin hydration between two lanolin-containing foams and "no treatment".

Controlled Study, to Assess the Skin Hydration of Two Lanolin Based Foam Compositions Six subjects were treated with foam compositions LAN1 and LAN2, on their arm. Skin hydration was measured using Corneometer CM825 for 240 minutes (6 hours) at the treatment sites and at an untreated site. The skin hydration values for the two lanolin based foams vs. "no treatment" is presented in Table 1 below and is shown in FIG. 1. Table 2 provides the "delta" values, i.e., the difference between the hydration effect of LAN1 and LAN 2, and the hydration value of the non-treated sites, which is illustrated in FIG. 2. As demonstrated in Tables 1 and 2, LAN1 and LAN2 foams provided significant hydration for at least 6 hours. The improvement rendered by LAN1 was in the range of 16.7%-22.4%, and for LAN2, there was a 24.9%-19.6% improvement. For comparison purposes, in a parallel group, which was treated with a commercial 12% ammonium lactate lotion, the skin moisture was improved by 20%-28%. Notable, while 12% ammonium lactate is a prescription drug with known side effects, the lanolin foam compositions can be generally considered as safe and can be used daily without safety concerns.

TABLE 1

Moisturizing Test: Two Lanolin Based Foams vs. No Treatment, using Corneometer CM825

|  | Corneometer CM825 Values | | |
|---|---|---|---|
| Time (min) | No Treatment | LAN1 | LAN2 |
| 0 | 41 | 40 | 38 |
| 60 | 41 | 48 | 47 |
| 120 | 40 | 47 | 49 |
| 180 | 40 | 47 | 49 |
| 240 | 42 | 49 | 49 |

TABLE 2

Moisturizing Test: The Absolute (Incremental) Skin Hydrating Effect of Two Lanolin, Using Corneometer CM825

|  | Corneometer CM825 Values | |
|---|---|---|
| Time (min) | LAN1 | LAN2 |
| 60 | 7.75 (+19.4%) | 9.46 (+24.9%) |
| 120 | 6.71 (+16.7%) | 11.04 (+29.1%) |
| 180 | 6.75 (+16.9%) | 11.25 (+29.6%) |
| 240 | 8.96 (+22.4%) | 11.21 (+29.5%) |

What is claimed is:

1. A hydrating foamable composition comprising an emulsion, the emulsion comprising:
   i. a hydrating component comprising lanolin, wherein the lanolin is present in an amount of at least about 5% by weight of the composition emulsion;
   ii. about 0.1% to about 5% of a non-ionic surface-active agent by weight of the composition emulsion;
   iii. about 0.01% to about 5% by weight of the emulsion of at least one polymeric additive selected from the group consisting of a bioadhesive agent, a gelling agent, a film forming agent~and a phase change agent;
   iv. water; and
   v. at least one therapeutic agent selected from the group consisting of an anti-infective, an antibiotic, an antibacterial agent, an antifungal agent, an antiviral agent, an antiparasitic agent, a steroidal antiinflammatory agent, an immunosuppressive agent, an immunomodulator, an immunoregulating agent, a hormonal agent, a vitamin A, a vitamin A derivative, a vitamin B, a vitamin B derivative, a vitamin C, a vitamin C derivative, a vitamin D, a vitamin D derivative, a vitamin E, a vitamin E derivative, a vitamin F, a vitamin F derivative, a vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzol chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, a skin whitening agent, a skin protective agent, a masking agent, an anti-wart agent, a refatting agent, a lubricating agent, and mixtures of two or more thereof; and a liquefied or compressed gas propellant at a concentration of about 3% to about 25% by weight of the total composition;

wherein the composition is free of ionic surface active agents; and wherein upon release from a pressurized container the composition expands to form a breakable foam that is thermally stable and collapses upon application of shear force.

2. The foamable composition of claim 1, further comprising at least one organic carrier selected from the group consisting of a hydrophobic organic carrier, a polar solvent, an emollient, and mixtures of two or more thereof, wherein the at least one organic carrier is present in an amount selected from the group consisting of (i) about 2% to about 5% by weight of the emulsion; (ii) about 5% to about 10% by weight of the emulsion; (iii) about 10% to about 20% by weight of the emulsion; and (iv) about 20% to about 50% by weight of the emulsion.

3. The foamable composition of claim 1, further comprising about 0.1% to about 5% by weight of the emulsion of a therapeutically active foam adjuvant selected from the group consisting of a fatty alcohol having 15 or more carbons in their carbon chain; a fatty acid having 16 or more carbons in their carbon chain; fatty alcohols derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; and a fatty acid substituted with a hydroxyl group, and mixtures of two or more thereof.

4. The foamable composition of claim 1, wherein the foamable composition is substantially free of short chain alcohols.

5. The foamable composition of claim 1, wherein the lanolin is selected from the group consisting of:
i. lanolin, wool fat, lanolin wax, and a synthetic lanolin;
ii. a synthetic lanolin comprising at least one of cholesterol, isocholesterol, and analogs, derivatives, salts, and esters thereof;
iii. an oil-soluble hydrophobic derivative of lanolin;
iv. a synthetic lanolin comprising at least one of cholesterol and isocholesterol covalently linked with an organic moiety;
v. a synthetic lanolin comprising at least one of cholesterol and isocholesterol covalently linked with an aliphatic acid;
vi. a lanolin acid;
vii. an ester of lanolin acid with an aliphatic alcohol; and
viii. a compound selected from the group consisting of acetylated lanolin, isopropyl lanolate, and cetyl lanolate.

6. The foamable composition of claim 1, wherein the concentration range of lanolin is selected from the group of (i) between about 5% and about 12% by weight of the emulsion; and (ii) between about 12% and about 24% by weight of the emulsion.

7. The foamable composition of claim 1, wherein the concentration of the non-ionic surface active agent is less than about 2% by weight of the emulsion.

8. The foamable composition of claim 1, wherein the emulsion is a water in oil emulsion.

9. The foamable composition of claim 1, wherein the emulsion is an oil in water emulsion.

10. The foamable composition of claim 1, wherein the non-ionic surface active agent comprises a combination of at least one non-ionic surfactant having HLB of less than 9 and at least one non-ionic surfactant having HLB of equal or more than 9, wherein the ratio between the at least one non-ionic surfactant having HLB of less than 9 and the at least one non-ionic surfactant having HLB of equal or more than 9, is between 1:8 and 8:1.

11. The foamable composition of claim 1, wherein the polymeric agent is selected from the group consisting of a water-soluble cellulose ether, a naturally-occurring polymeric material, and mixtures of two or more thereof.

12. The foamable composition of claim 1, wherein the polymeric agent is selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose, carboxymethylhydroxyethylcellulose, xanthan gum, guar gum, carrageenan gum, locust bean gum, and tragacanth gum.

13. A method of treating or alleviating insufficient hydration of skin, a body cavity or a mucosal surface, comprising:
administering topically to skin, a body cavity or a mucosal surface a breakable foam that is thermally stable and collapses upon application of shear force, wherein the foam is obtained by releasing from a pressurized container a foamable composition comprising an emulsion comprising:
a) a hydrating component comprising lanolin, wherein the lanolin is present in an amount of at least about 5% by weight of the composition emulsion;
b) about 0.1% to about 5% of a non-ionic surface-active agent by weight of the composition emulsion;
c) about 0.01% to about 5% by weight of the emulsion of at least one polymeric additive selected from the group consisting of a bioadhesive agent, a gelling agent, a film forming agent~and a phase change agent; and
d) water; and
a liquefied or compressed gas propellant at a concentration of about 3% to about 25% by weight of the total composition;
wherein the non-ionic surface active agent comprises a combination of at least one non-ionic surfactant having HLB of less than 9 and at least one non-ionic surfactant having HLB of equal or more than 9, wherein the ratio between the at least one non-ionic surfactant having HLB of less than 9 and the at least one non-ionic surfactant having HLB of equal or more than 9, is between 1:8 and 8:1;

wherein the composition is free of ionic surface active agents.

14. The method of claim 13, wherein the composition further comprises about 0.1% to about 5% by weight of the emulsion of a therapeutically active foam adjuvant selected from the group consisting of a fatty alcohol having 15 or more carbons in their carbon chain; a fatty acid having 16 or more carbons in their carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group and mixtures thereof~and mixtures of two or more thereof.

15. The method of claim 13 or 14, wherein the composition further comprises an additional active agent effective to treat a disorder of skin, a body cavity or a mucosal surface.

16. The method of claim 13, wherein the foamable composition further comprises at least one component, selected from (1) a therapeutically effective foam adjuvant and (2) an organic carrier consisting of at least one therapeutically active oil.

17. The method of claim 13, wherein the foamable composition further comprises a therapeutically effective foam adjuvant and an organic carrier consisting of at least one therapeutically active oil.

18. A hydrating foamable composition comprising an emulsion, the emulsion comprising:
   i. a hydrating component comprising lanolin, wherein the lanolin is present in an amount of at least about 5% by weight of the emulsion;
   ii. about 0.1% to about 5% of a non-ionic surface-active agent by weight of the emulsion;
   iii. about 0.01% to about 5% by weight of the emulsion of at least one polymeric additive selected from the group consisting of a bioadhesive agent, a gelling agent, a film forming agent, and a phase change agent; and
   iv. water; and
   a liquefied or compressed gas propellant at a concentration of about 3% to about 25% by weight of the total composition;
   wherein the non-ionic surface active agent comprises a combination of at least one non-ionic surfactant having HLB of less than 9 and at least one non-ionic surfactant having HLB of equal or more than 9, wherein the ratio between the at least one non-ionic surfactant having HLB of less than 9 and the at least one non-ionic surfactant having HLB of equal or more than 9, is between 1:8 and 8:1;
   wherein the composition is free of ionic surface active agents; and
   wherein upon release from a pressurized container the composition expands to form a breakable foam that is thermally stable and collapses upon application of shear force.

19. The foamable composition of claim 18, further comprising at least one organic carrier selected from the group consisting of a hydrophobic organic carrier, a polar solvent, an emollient, and mixtures of two or more thereof, wherein the at least one organic carrier is present in an amount selected from the group consisting of (i) about 2% to about 5% by weight of the emulsion; (ii) about 5% to about 10% by weight of the emulsion; (iii) about 10% to about 20% by weight of the emulsion; and (iv) about 20% to about 50% by weight of the emulsion.

20. The foamable composition of claim 18, further comprising about 0.1% to about 5% by weight of the emulsion of a therapeutically active foam adjuvant selected from the group consisting of a fatty alcohol having 15 or more carbons in their carbon chain; a fatty acid having 16 or more carbons in their carbon chain; fatty alcohols derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; and mixtures of two or more thereof.

21. The foamable composition of claim 18, wherein the foamable composition is substantially free of short chain alcohols.

22. The foamable composition of claim 18, wherein the lanolin is selected from the group consisting of:
   i. lanolin, wool fat, lanolin wax, and a synthetic lanolin;
   ii. a synthetic lanolin comprising at least one of cholesterol, isocholesterol, and analogs, derivatives, salts, and esters thereof;
   iii. an oil-soluble hydrophobic derivative of lanolin;
   iv. a synthetic lanolin comprising at least one of cholesterol and isocholesterol covalently linked with an organic moiety;
   v. a synthetic lanolin comprising at least one of cholesterol and isocholesterol covalently linked with an aliphatic acid;
   vi. a lanolin acid;
   vii. an ester of lanolin acid with an aliphatic alcohols; and
   viii. a compound selected from the group consisting of acetylated lanolin, isopropyl lanolate, and cetyl lanolate.

23. The foamable composition of claim 18, wherein the concentration range of lanolin is selected from the group of (i) between about 5% and about 12% by weight of the emulsion; and (ii) between about 12% and about 24% by weight of the emulsion.

24. The foamable composition of claim 18, further comprising at least one additional therapeutic agent selected from the group consisting of an anti-infective, an antibiotic, an antibacterial agent, an antifungal agent, an antiviral agent, an antiparasitic agent, a steroidal antiinflammatory agent, an immunosuppressive agent, an immunomodulator, an immunoregulating agent, a hormonal agent, a vitamin A, a vitamin A derivative, a vitamin B, a vitamin B derivative, a vitamin C, a vitamin C derivative, a vitamin D, a vitamin D derivative, a vitamin E, a vitamin E derivative, a vitamin F, a vitamin F derivative, a vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, an allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, an anti wrinkle agent, a skin whitening agent, a skin protective agent, a masking agent, an anti-wart agent, a refatting agent, a lubricating agent, and mixtures of two or more thereof.

25. The foamable composition of claim 18, wherein the concentration of the non-ionic surface active agent is less than about 2% by weight of the emulsion.

26. The foamable composition of claim 18, wherein the emulsion is a water in oil emulsion.

27. The foamable composition of claim 18, wherein the emulsion is an oil in water emulsion.

28. The foamable composition of claim 18, wherein the polymeric agent is selected from the group consisting of a water-soluble cellulose ether, a naturally-occurring polymeric material, and mixtures of two or more thereof.

29. The foamable composition of claim 18, wherein the polymeric agent is selected from the group consisting of methylcellulose, hydroxypropyl cellulose, hydroxypropyl methylcellulose (Methocel), hydroxyethyl cellulose, methylhydroxyethylcellulose, methylhydroxypropylcellulose, hydroxyethylcarboxymethylcellulose, carboxymethylcellulose, carboxymethylhydroxyethylcellulose, xanthan gum, guar gum, carrageenan gum, locust bean gum, and tragacanth gum.

30. A method of administering a therapeutic agent to skin, a body cavity, or a mucosal surface comprising: administering topically to the skin, body cavity or mucosal surface a breakable foamed composition that is thermally stable and collapses upon application of shear force, wherein the foam is obtained by, releasing from a pressurized container a foamable composition comprising an emulsion comprising:
  a) a hydrating component comprising lanolin, wherein the lanolin is present in an amount of at least about 5% by weight of the emulsion;
  b) about 0.1% to about 5% of a non-ionic surface-active agent by weight of the emulsion;
  c) about 0.01% to about 5% by weight of the emulsion of at least one polymeric additive selected from the group consisting of a bioadhesive agent, a gelling agent, a film forming agent and a phase change agent;
  d) at least one therapeutic agent selected from the group consisting of an anti-infective, an antibiotic, an antibacterial agent, an antifungal agent, an antiviral agent, an antiparasitic agent, an steroidal antiinflammatory agent, an immunosuppressive agent, an immunomodulator, an immunoregulating agent, a hormonal agent, a vitamin A, a vitamin A derivative, a vitamin B, a vitamin B derivative, a vitamin C, a vitamin C derivative, a vitamin D, a vitamin D derivative, a vitamin E, a vitamin E derivative, a vitamin F, a vitamin F derivative, a vitamin K, a vitamin K derivative, a wound healing agent, a disinfectant, an anesthetic, an antiallergic agent, an alpha hydroxyl acid, lactic acid, glycolic acid, a beta-hydroxy acid, a protein, a peptide, a neuropeptide, a allergen, an immunogenic substance, a haptene, an oxidizing agent, an antioxidant, a dicarboxylic acid, azelaic acid, sebacic acid, adipic acid, fumaric acid, a retinoid, an antiproliferative agent, an anticancer agent, a photodynamic therapy agent, benzoyl chloride, calcium hypochlorite, magnesium hypochlorite, an anti-wrinkle agent, a radical scavenger, a metal, silver, a metal oxide, titanium dioxide, zinc oxide, zirconium oxide, iron oxide, silicone oxide, talc, carbon, a skin whitening agent, a skin protective agent, a masking agent, an anti-wart agent, a refatting agent, a lubricating agent, and mixtures of two or more thereof; and
  e) water; and
  a liquefied or compressed gas propellant at a concentration of about 3% to about 25% by weight of the total composition;
  wherein the composition is free of ionic surface active agents.

31. The method of claim 30, wherein the composition further comprises about 0.1% to about 5% by weight of the emulsion of a therapeutically active foam adjuvant selected from the group consisting of a fatty alcohol having 15 or more carbons in their carbon chain; a fatty acid having 16 or more carbons in their carbon chain; fatty alcohols, derived from beeswax and including a mixture of alcohols, a majority of which has at least 20 carbon atoms in their carbon chain; a fatty alcohol having at least one double bond; a fatty acid having at least one double bond; a branched fatty alcohol; a branched fatty acid; a fatty acid substituted with a hydroxyl group; and mixtures of two or more thereof.

32. The method of claim 30 or 31, wherein the composition further comprises an additional active agent effective to treat a disorder of skin, a body cavity or a mucosal surface.

33. The method of claim 30, wherein the foamable composition further comprises at least one component, selected from (1) a therapeutically effective foam adjuvant and (2) an organic carrier consisting of at least one therapeutically active oil.

34. The method of claim 30, wherein the foamable composition further comprises a therapeutically effective foam adjuvant and an organic carrier consisting of at least one therapeutically active oil.

35. The foamable composition of claim 1, wherein the concentration of the non-ionic surface active agent is less than about 1% by weight of the emulsion.

36. The foamable composition of claim 18, wherein the concentration of the non-ionic surface active agent is less than about 1% by weight of the emulsion.

* * * * *

UNITED STATES PATENT AND TRADEMARK OFFICE
CERTIFICATE OF CORRECTION

PATENT NO. : 8,486,376 B2  
APPLICATION NO. : 11/099942  
DATED : July 16, 2013  
INVENTOR(S) : Doron Friedman et al.

Page 1 of 1

It is certified that error appears in the above-identified patent and that said Letters Patent is hereby corrected as shown below:

On the title page

Item 75 (inventors), please delete "Rehovet" and insert -- Rehovot --, therefor.

In the claims

Column 14, Line 64 (Claim 1), please delete "agent~and" and insert -- agent, and --, therefor.

Column 15, Line 12 (Claim 1), please delete "a allergen" and insert -- an allergen --, therefor.

Column 15, Line 18 (Claim 1), please delete "benzo1" and insert -- benzoyl --, therefor.

Column 16, Line 58 (Claim 13), please delete "agent~and" and insert -- agent, and --, therefor.

Column 17, Line 18 (Claim 14), please delete "group and mixtures thereof~" and insert -- group; --, therefor.

Column 18, Line 35 (Claim 21), please delete "alcohols" and insert -- alcohol --, therefor.

Column 19, Line 45 (Claim 30), please delete "vitamin derivative," and insert -- vitamin E derivative, --, therefor.

Column 19, Line 50 (Claim 30), please delete "a allergen" and insert -- an allergen --, therefor.

Signed and Sealed this  
Twenty-fourth Day of June, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,486,376 B2 | Page 1 of 1 |
| APPLICATION NO. | : 11/099942 | |
| DATED | : July 16, 2013 | |
| INVENTOR(S) | : Friedman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1799 days.

Signed and Sealed this
Third Day of March, 2015

Michelle K. Lee
*Deputy Director of the United States Patent and Trademark Office*